US005821118A

United States Patent [19]
Omer et al.

[11] Patent Number: 5,821,118
[45] Date of Patent: Oct. 13, 1998

[54] GENES FOR THE SUBUNITS OF HUMAN FARNESYL-PROTEIN TRANSFERASE

[75] Inventors: Charles A. Omer, Lansdale; Ronald E. Diehl, Line Lexington; Jackson B. Gibbs, Chalfont; Nancy E. Kohl, Wyndmoor, all of Pa.

[73] Assignee: Merck & Co., Inc., Rahway, N.J.

[21] Appl. No.: 424,268

[22] PCT Filed: Oct. 29, 1993

[86] PCT No.: PCT/US93/10442

§ 371 Date: Apr. 24, 1995

§ 102(e) Date: Apr. 24, 1995

[87] PCT Pub. No.: WO94/10184

PCT Pub. Date: May 11, 1994

Related U.S. Application Data

[63] Continuation of Ser. No. 968,782, Oct. 30, 1992, abandoned.

[51] Int. Cl.$^6$ .............................. C12N 1/21; C12N 9/10; C12N 15/54
[52] U.S. Cl. ........................ 435/320.1; 435/15; 435/193; 435/252.3; 435/252.33; 536/23.2
[58] Field of Search ........................ 435/15, 69.1, 172.1, 435/193, 252.3, 320.1, 172.3, 252.33; 536/23.2

[56] References Cited

U.S. PATENT DOCUMENTS

| | | | |
|---|---|---|---|
| 5,141,851 | 8/1992 | Brown et al. | 435/15 |
| 5,185,248 | 2/1993 | Barbacid et al. | 435/15 |
| 5,420,245 | 5/1995 | Brown et al. | 530/328 |

FOREIGN PATENT DOCUMENTS

| | | |
|---|---|---|
| 0456180 | 11/1991 | European Pat. Off. . |
| 0461869 | 12/1991 | European Pat. Off. . |
| WO 91/16340 | 10/1991 | WIPO . |
| WO 94/04561 | 3/1994 | WIPO . |

OTHER PUBLICATIONS

Chen, W–J. et al., "cDNA Cloning and Expression of the Peptide–Binding B Subunit of Rat p21ras Farnesyltransferase, the Counterpart of Yeast DPR1/RAM1", Cell, vol. 66, pp. 327–334 (1991).

Chen, W–J., Cloning and expression of a cDNA encoding the a subunit of rat p21ras protein farnesyltransferase, PNAS USA, vol. 88, pp. 11368–11372 (1991).

Gibbs, J.B. and Marshall, M.S., "The ras Oncogene–an Important Regulatory Element in Lower Eucaryotic Organisms", Microbiol. Review, vol. 53, pp. 171–185 (1989).

Gold, L. and Stormo, G.D., "High–Level Translation Initiation", Methods in Enzymology, vol. 185, pp. 89–93 (1990).

Goldstein, J.L., et al., "Nonfarnesylated Tetrapeptide Inhibitors of Protein Farnesyltransferase", J. Biol. Chem., vol. 266, pp. 15575–15578, (1991).

He, B., et al., "RAM2, an essential gene of yeast, and RAM1 encode the two polypeptide components of the famesytrasferase that prenylates a–factor and Ras proteins", Proc. Natl. Acad. Sci. USA, vol. 88, pp. 11373–11377 (1991).

Kohl, N.E. et al., "Structural Homology among Mammalian and *Sccharomyces cerevisiae* Isoprenyl–protein Transferases", The Journ. of Biol. Chem., vol. 266, No. 28, pp. 18884–18888 (1991).

Manne, V., et al., "Identification and preliminary characterization of protein–cysteine farnesyltransferase", Proc. Natl. Acad. Sci. USA, vol. 87, pp. 7541–7545 (1990).

Moores, S.L., et al., "Sequence Dependence of Protein Isoprenylation", The Jour. of Biol. Chem., vol. 266, pp. 14603–14610 (1991).

Pompliano, D.L., et al., "Steady–State Kinetic Mechanism of Ras Farnesyl: Protein Transferase", Biochemistry, vol. 31, pp. 3800–3807 (1992).

Reiss, Y., "Inhibition of Purified p21ras Farnesyl:Protein Transferase by Cys–AAX Tetrapeptides", Cell, vol. 62, pp. 81–88 (1990).

Reiss, Y., "Nonidentical Subunits of p21 H–ras Farnesyltransferase", The Jour. of Biol. Chem., vol. 266, No. 16, pp. 10672–10677 (1991).

Schaber, M.D., et al., "Polyisoprenylation of Ras in Vitro by a Farnesyl–Protein Transferase", The Journ. of Biol. Chem., vol. 365, No. 25, pp. 14701–14704 (1990).

Schoner, B.E., et al., "Enhanced Translational Efficiency with Two–Cistron Expression System", Methods in Enzymology, vol. 185, pp. 94–103 (1990).

Stammers, D.K., et al., "Rapid purification and characterisation of HIV–1 reverse transcriptase and RNaseH engineered to incorporate a C–terminal tripeptide a–tubulin epitope", FEBS, vol. 283, No. 2, pp. 298–302 (1991).

Willumsen, B.M. and Christensen, A., "The p21 ras C–terminus is required for transformationand membrane association", Naure, vol. 310, pp. 583–586 (1984).

Willumsen, B.M., et al., "Harvey murine sarcoma virus p21 ras protein: biological and biochemical significance of the cysteine nearest the carboxy terminus", EMBO, vol. 3, No. 11, pp. 2581–2585 (1984).

Vogel, U.S., et al., "Cloning of bovine GAP and its interaction with oncogenic ras p21", Nature, vol. 335, pp. 90–93 (1988).

Goodman, L.E., et al., "Structure and Expression of Yeast DPR1, a Gene Essential for the Processing and Intracellular Localization of ras Proteins", Yeast, vol. 4, pp. 271–281 (1988).

Andres, D.A., et al., "Mutational Analysis of a–Subunit of Protin Farnesyltransferase", The Jour. of Biol. Chem., vol. 268, pp. 1383–1390 (1993).

Novagen catalog (1991) pp. 27–28.

*Primary Examiner*—Dian C. Jacobson
*Attorney, Agent, or Firm*—David A. Muthard; Mark R. Daniel

[57] ABSTRACT

The present invention relates to an assay useful in determining the farnesyl-protein transferase inhibitory activity of pharmaceutical agents. The assay employs purified human farnesyl-protein transferase which is prepared by gene expression in *Escherichia coli*.

6 Claims, 15 Drawing Sheets

```
1    ATGGCTTCTCCGAGTTCCTTCACTTACTGTTGCCCTCCATCTTCCTCCCCTATCTGGTCA
     MetAlaSerProSerSerPheThrTyrCysCysProProSerSerProIleTrpSer         20

61   GAACCGCTGTACAGTCTGAGGCCAGAGCACGCGGGAGCGGTTGCAGGACGACTCGGTG
     GluProLeuTyrSerLeuArgProGluHisAlaArgGluArgLeuGlnAspAspSerVal      40

121  GAAACAGTCACGTCCATAGAACAGGCAAAAGTAGAAGAAAGATCCAAGAGGTCTTCAGT
     GluThrValThrSerIleGluGlnAlaLysValGluGluLysIleGlnGluValPheSer      60

181  TCTTACAAGTTCAACCACCTGTACCAAGGCTTGTTTTGCAGAGAGAAGCACTTCCAT
     SerTyrLysPheAsnHisLeuValProArgLeuValLeuGlnArgGluLysHisPheHis      80

241  TATCTGAAAAGAGGCCTCCGACAGCTACGAGTGTCTGGATGCCAGCCGC
     TyrLeuLysArgGlyLeuArgGlnLeuThrAspAlaTyrGluCysLeuAspAlaSerArg     100

301  CCATGGCTCTGCTACTGGATCCTGCATAGCCTCCTGGAACTCCTGGAGCCCATCCCCAG
     ProTrpLeuCysTyrTrpIleLeuHisSerLeuLeuGluLeuLeuAspGluProIleProGln  120

361  ATGGTGGCCACAGACGTGTCAGTTCCTGGAGTTGTGTCAGAGCCCAGAAGGCGGCTTT
     MetValAlaThrAspValCysGlnPheLeuGluLeuCysGlnSerProGluGlyGlyPhe     140

421  GGAGGGGCCCTGCCCAGTACCCACCTTGCACCCACACTATGCCAGGCGGTCAACGGCTG
     GlyGlyGlyProGlyGlnTyrProHisLeuAlaProThrTyrAlaAlaValAsnAlaLeu     160

481  TGCATCATTGGCACCGAGAGGCCTATGACGTCATTAACAGAGAAGCTTCTCCAGTAT
     CysIleIleGlyThrGluGluAlaTyrAspValIleAsnArgGluLysLeuLeuGlnTyr     180
```

FIG.1A

```
 541  TTGTACTCGCTGAAGCAACCCGATGGCTCTTTTCTCATGCACGATGGAGGTGAGTGGAC
      LeuTyrSerLeuLysGlnProAspGlySerPheLeuMetHisAspGlyGlyGluValAsp  200

601  GTGAGAAGTGCATACTGTCTGCCTCGGTAGCTTCGTTGACCAACATCATCACCCCAGAC
      ValArgSerAlaTyrCysAlaAlaSerValAlaSerLeuThrAsnIleIleThrProAsp  220

661  CTGTTTGAGGGCACTGCTGAATGCAAGGTGTCAGAATTGGAAGGTGGATTGGC
      LeuPheGluGlyThrAlaGluTrpIleAlaArgCysGlnAsnTrpGluGlyGlyIleGly  240

721  GGGGTACCAGGAATGGAAGCCCATGGCGGCTACACGTTCTGTGGCCTGGCTGCCTGGTC
      GlyValProGlyMetGluAlaHisGlyGlyTyrThrPheCysGlyLeuAlaAlaLeuVal  260

781  ATCCTCAAGAAGGAGGCTCCTGAACTTGAAGAGCTTACTACAATGGGTACAAGCCGG
      IleLeuLysLysGluArgSerLeuAsnLeuLysSerLeuLeuGlnTrpValThrSerArg  280

841  CAGATGAGGTTTGAAGGTGGATTTCAGGGCTTCAGGGCTACGACGGCTAC
      GlnMetArgPheGluGlyGlyPheGlnGlyArgCysAsnLysLeuValAspGlyCysTyr  300

901  TCCTTCTGGCAGGCATGTCGCTGCTCCTGCCCCTGCTTCACCCGCGCCAAGGTGAC
      SerPheTrpGlnAlaGlyLeuLeuProLeuLeuHisArgAlaLeuHisAlaGlnGlyAsp  320

961  CCTGCCCTCAGCATGAGTCGCTGATGTTCACCAGCCCTGCCAGGAGTACATCCTG
      ProAlaLeuSerMetSerArgTrpMetPheHisGlnGlnAlaLeuGlnTyrIleLeu  340

1021  ATGTGCTGCCAGTGCCCACCGGGGCTTCTGGACAAACCTGCAAGTCCCGGACTTC
      MetCysCysGlnCysProThrGlyLeuLeuAspLysProGlyLysSerArgAspPhe  360
```

FIG.1B

```
1081  TACCACACCTGCTACTGCCTGAGTGGCCTGTCCATAGCCCAGCACTTCGGCAGCGGAGCC
      TyrHisThrCysTyrCysLeuSerGlyLeuSerIleAlaGlnHisPheGlySerGlyAla  380

1141  ATGTTGCACGATGTGGTCTTGGGTGTACCTGAAAACGCCCTGCAGCCCACTCACCCTGTG
      MetLeuHisAspValValLeuGlyValProGluAsnAlaLeuGlnProThrHisProVal  400

1201  TACAATATTGGACCAGACAAAGTGATCGGCAGGTACCATGCACTTTCTGCAGAAGCCAGTT
      TyrAsnIleGlyProAspLysValIleGlnAlaThrMetHisPheLeuGlnLysProVal  420

1261  CCAGGCTTTGAGGAGCATGAGGATGAGGCATCAGCAGAGCCTGCCACTGACTAG
      ProGlyPheGluGluHisGluAspGluAlaSerAlaGluProAlaThrAspEnd  437
```

FIG.1C

```
  1  ATGGGGGCCACCGAGGGGGTCGGGGAGGCTGCCAAGGGGGCGGAGCCCGGCG        20
     MetAlaAlaThrGluGlyValGlyGluAlaAlaGlnGlyGlyGluProGlyProAla

61  CAACCCCCGCCCCAGCCGCACCGCGCCGCCAGCAGCAGCAGCAAGGAGAGATGGCG      40
     GlnProProProGlnProHisProProProGlnGlnGlnHisLysGluGluMetAla

121  GCCGAGGCTGGGGAAGCCGTGGCCGTCCCCCATGGACGACGGGTTTGTGAGCCTGGACTCG  60
     AlaGluAlaGlyGluAlaValAlaValProMetAspAspGlyPheValSerLeuAspSer

181  CCCTCCTATGTCCTGTACAGGAGACAGAGCAGAATGGGGCTGATATAGATCCGGTGCCGCAG 80
     ProSerTyrValLeuTyrArgAspArgAlaGluTrpAlaAspIleAspProValProGln

241  AATGATGGCCCAATCCCGTCCAGATCATTTATAGTGACAAATTTAGATGTTAT         100
     AsnAspGlyProAsnProValValGlnIleIleTyrSerAspLysPheArgAspValTyr

301  GATTACTTCCGAGCTGTCCTGCAGCGTGATGAAAGAAGTGAACGAGCTTTTAAGCTAACC   120
     AspTyrPheArgAlaValLeuGlnArgAspGluArgSerGluArgAlaPheLysLeuThr

361  CGGGATGCTATTGAGTTAAATGCAGCCAATTATACAGTGTGCCATTTCCGGAGAGTTCTT  140
     ArgAspAlaIleGluLeuAsnAlaAlaAsnTyrThrValTrpHisPheArgArgValLeu
```

FIG.2A

```
421  TTGAAGTCACTTCAGAAGGATCTACATGAGGAAATGAACTACACTCACTGCAATAATTGAG
     LeuLysSerLeuGlnLysAspLeuHisGluGluMetAsnTyrIleThrAlaIleIleGlu   160

481  GAGCAGCCCAAAAACTATCAAGTTGGCATCATAGGCGAGTATTAGTGGAATGGCTAAGA
     GluGlnProLysAsnTyrGlnValTrpHisHisArgArgValLeuValGluTrpLeuArg   180

541  GATCCATCTCAGGAGCTTGAATTTATTGCTGATATTCTTAATCAGGATGCAAAGAATTAT
     AspProSerGlnGluLeuGluPheIleAlaAspIleLeuAsnGlnAspAlaLysAsnTyr   200

601  CATGCCTGGCAGCATCGACAATGGTTATTCAGGAATTAAACTTTGGGATAATGAGCTG
     HisAlaTrpGlnHisArgGlnTrpValIleGlnPheLysLeuTrpAspAsnGluLeu     220

661  CAGTATGTGGACCAACTTCTGAAAGAGGATGTGAGAAATAACTCTGTCTGGAACCAAAGA
     GlnTyrValAspGlnLeuLeuLysGluAspValArgAsnAsnSerValTrpAsnGlnArg  240

721  TACTTCGTTATTCTAACACCACTGGCTACAATGATCGTGCTGTATTGGAGAGAAGTC
     TyrPheValIleSerAsnThrThrGlyTyrAsnAspArgAlaValLeuGluArgGluVal  260
```

FIG.2B

```
781   CAATACACTCTGGAAATGATTAAACTAGTACCACATAATGAAAGTGCATGGAACTATTTG
      GlnTyrThrLeuGluMetIleLysLeuValProHisAsnGluSerAlaTrpAsnTyrLeu  280

841   AAAGGGATTTGCAGGATCGTGTCTTTCCAAATATCCTAATCTGTTAAATCAATTACTT
      LysGlyIleLeuGlnAspArgGlyLeuSerLysTyrProAsnLeuLeuAsnGlnLeuLeu  300

901   GATTTACAACCAAGTCATAGTTCCCCTACCTAATTGCCTTTCTCTGTGGATATCTATGAA
      AspLeuGlnProSerHisSerProTyrLeuIleAlaPheLeuValAspIleTyrGlu     320

961   GACATGCTAGAAATCAGTGTGACAATAAGGAAGACATTCTTAATAAAGCATTAGAGTTA
      AspMetLeuGluAsnGlnCysAspAsnLysGluAsnLysIleLeuAsnLysAlaLeuGluLeu  340

1021  TGTGAAATCCTAGCTAAAGAAAGGACACTATAAGAAAGGAATATTGGAGATACATTGGA
      CysGluIleLeuAlaLysGluLysAspThrIleArgLysGluTyrTrpArgTyrIleGly  360

1081  AGATCCCTTCAAAGCAAACACAGCACAGAAAATGACTCACCAACAAATGTACAGCAATAA
      ArgSerLeuGlnSerLysHisSerThrGluAsnAspSerProThrAsnValGlnGlnEnd  379
```

FIG.2C

```
  1   ATGGCTTCTCCGAGTTCTTTCACCTACTATTGCCCTCCATCTTCCTCCCCGTCTGGTCA
      MetAlaSerProSerSerPheThrTyrTyrCysProProSerSerProValTrpSer    20

61   GAGCCGCTGTACAGTCTGAGCCCGAGCACGCGCGAGAGCGGTTGCAGACGACTCGGTG
      GluProLeuTyrSerLeuArgProGluHisAlaArgGluArgLeuGlnAspAspSerVal  40

121   GAAACAGTCACGTCCATAGAACAGGCAAAAGTAGAAGAAAAGATCCAAGAGGTCTTCAGT
      GluThrValThrSerIleGluGlnAlaLysValGluGluLysIleGlnGluValPheSer  60

181   TCTTACAAGTTCAACCACCTTGTACCAAGGCTTGTTTTGCAGAGGGAGAAGCACTTCCAT
      SerTyrLysPheAsnHisLeuValProArgLeuValLeuGlnArgGluLysHisPheHis  80

241   TATCTGAAAAGAGGCCTTGACAACTGACAGATGCCTATGAGTGTCTGGATGCCAGCCGC
      TyrLeuLysArgGlyLeuAspAsnLeuThrAspAlaTyrGluCysLeuAspAlaSerArg 100

301   CCATGGCTCTGCTATTGGATCCTGCACAGCTTGAACTGCTAGATGAACCCATCCCCCAG
      ProTrpLeuCysTyrTrpIleLeuHisSerLeuGluLeuLeuAspGluProIleProGln 120

361   ATAGTGGCTACAGATGTGTGTCAGTTCCTGGAGCTGTGTCAGAGCCCAGAAGGTGGCTTT
      IleValAlaThrAspValCysGlnPheLeuGluLeuCysGlnSerProGluGlyGlyPhe 140

421   GGAGGAGGACCCGGTCAGTATCCACACCTTGCACCCACATATCAGCAGTCAATGCATTG
      GlyGlyGlyProGlyGlnTyrProHisLeuAlaProThrTyrAlaAlaValAsnAlaLeu 160

481   TGCATCATTGGCACCGAGGCCTATGACATCATTAACAGAGAAGTTCTTCAGTAT
      CysIleIleGlyThrGluAlaTyrAspIleIleAsnArgGluLysLeuLeuGlnTyr     180
```

FIG. 3A

```
541   TTGTACTCCCTGAAGCAACCTGACGGCTCCTTTCTCATGCATGTCGGAGTGAGTGGAT
      LeuTyrSerLeuLysGlnProAspGlySerPheLeuMetHisValGlyGlyGluValAsp  200

601   GTGAGAAGGCGCATACTGTGCTGCCTAGCCTCCGTAGCCTCGACCAACATCATCACTCCAGAC
      ValArgSerAlaTyrCysAlaAlaSerValAlaSerLeuThrAsnIleIleThrProAsp  220

661   CTCTTTGAGGGCACTGCTGAATGCATAGCAAGGTGTCAGAACTGGAAGTGGCATTGGC
      LeuPheGluGlyThrAlaGluTrpIleAlaArgCysGlnAsnTrpGluGlyGlyIleGly  240

721   GGGGTACCAGGGATGGAAGCCCATGGTGCTATACCTTCTGTGGCCTGGCCGCGCTGTA
      GlyValProGlyMetGluAlaHisGlyGlyTyrThrPheCysGlyLeuAlaAlaLeuVal  260

781   ATCCTCAAGAGGAACGTTCCTGAACTTATTACAATGGTGACAAGCCGG
      IleLeuLysArgGluArgSerLeuAsnLeuLysSerLeuLeuGlnTrpValThrSerArg  280

841   CAGATGCGATTTGAAGGAGGATTTCAGGGCCGCTGCAACAAGCTGGTGATGGCTGTAC
      GlnMetArgPheGluGlyGlyPheGlnGlyArgCysAsnLysLeuValAspGlyCysTyr  300

901   TCCTTCTGGCAGGCGGGCTCCTGCCCCTGCTCCACCGCCACTGCACGCCCAAGTGAC
      SerPheTrpGlnAlaGlyLeuLeuProLeuLeuHisArgAlaLeuHisAlaGlnGlyAsp  320

961   CCTGCCCTTAGCATGAGCCACTGATGTTCCATCAGCCCTGCAGGAGTACATCCTG
      ProAlaLeuSerMetSerHisTrpPheHisGlnAlaLeuGlnGluTyrIleLeu  340

1021  ATGTGCTGCCAGTGCCCTGCGGGGGCTTCTGGATAAACCTGGCAAGTCGCGTGATTTC
      MetCysCysGlnCysProAlaGlyLeuGlyLeuLeuAspLysProGlyLysSerArgAspPhe  360
```

FIG. 3B

```
1081  TACCACACCTGCTACTGCCTGAGCGGCCTGTCCATAGCCCAGCACTTCGGCAGCGGAGCC
      TyrHisThrCysTyrCysLeuSerGlyLeuSerIleAlaGlnHisPheGlySerGlyAla  380

1141  ATGTTGCATGATGTGGTCCTGGGTGTGCCCGAAAACGCTCTGCAGCCCACTCACCCAGTG
      MetLeuHisAspValValLeuGlyValProGluAsnAlaLeuGlnProThrHisProVal  400

1201  TACAACATTGGACCAGACAAGGTGATCCAGGCCACTACATACTTTCTACAGAAGCCAGTC
      TyrAsnIleGlyProAspLysValIleGlnAlaThrThrTyrPheLeuGlnLysProVal  420

1261  CCAGGTTTTGAGGAGCTTAAGGATGAGACATCGGCAGAGCCTGCAACCGACTAG
      ProGlyPheGluGluLeuLysAspGluThrSerAlaGluProAlaThrAspEnd  437
```

FIG.3C

```
  1  GAATTCTAAGGAGGAAAAAAATGGCTTCTCCGAGTTCTTCAACTTACTATTGCCCTCC
                       M  A  S  P  S  S  F  T  Y  Y  C  P  P

61  ATCTTCTCCCCGTCTGTCAGAGCCGCTGTACAGTCTGAGCCCCTGTACTCTCTGAGACGGGCCGAGA
      S  S  S  P  V  W  S  E  P  L  Y  S  L  R  P  E  H  A  R  E

121  GCGGTTGCAGGAGGACTGGGTGAAACAGTCCATAGAACAGGCAAAAGTAGAAGA
      R  L  Q  D  D  S  V  E  T  V  T  S  I  E  Q  A  K  V  E  E

181  AAAGATCCAAGAGGTCTTCAGTTCTTCACAGTTCAACCACTTGTACCAGGCTTGTTT
      K  I  Q  E  V  F  S  S  Y  K  F  N  H  L  V  P  R  L  V  L

241  GCAGAGGGAGAAGCACTTCCATTATCTGAAAAGAGGCCTTGGACAACTGACAGATGCCTA
      Q  R  E  K  H  F  H  Y  L  K  R  G  L  R  Q  L  T  D  A  Y

301  TGAGTGTCTGGATCGGAGCCGCCCATGGCTCTGCTATTGGATCCTGCACAGCTTGGAACT
      E  C  L  D  R  S  R  P  W  L  C  Y  W  I  L  H  S  L  E  L

361  GCTAGATGAACCATCCCAGATAGTGGCTACAGATGTGTGTCAGTTCCTGGAGCTGTG
      L  D  E  P  I  P  Q  I  V  A  T  D  V  C  Q  F  L  E  L  C

421  TCAGACCCAGAAGGTGGCTTGGAGGAGGACCGGTCAGTATCCACACTTGCACCAC
      Q  S  P  E  G  G  F  G  G  G  P  G  Q  Y  P  H  L  A  P  T

481  ATATGCAGCAGTCAATGCATTGTGCATCATTGGCACCGAGGAGGCCTATGACATCATTAA
      Y  A  A  V  N  A  L  C  I  I  G  T  E  E  A  Y  D  I  I  N
```

FIG. 5A

541  CAGAGAGAAGCTTCTCAGTATTTGTACTCCCTGAAGCAACCTGAGGCTCTTTCTCAT
     R  E  K  L  L  Q  Y  L  Y  S  L  K  Q  P  D  G  S  F  L  M

601  GCATGTCGGAGGTGAGGTGGATGTGAGAGGCATACTGTCGTCCGTAGCCTCGCT
     H  V  G  G  E  V  D  V  R  S  A  Y  C  A  A  S  V  A  S  L

661  GACCAACATCATCACTCCAGACCTCTTTGAGGGCACTGCTGAATGATAGCAAGGTGTCA
     T  N  I  I  T  P  D  L  F  E  G  T  A  E  W  I  A  R  C  Q

721  GAACTGGAAGGTCCATTGCCGGGTACCAGGGATGAAGCCATGTGGCTATACTT
     N  W  E  G  G  I  G  G  V  P  G  M  E  A  H  G  G  Y  T  F

781  CTGTGGCCCTGGCCGCTGTATCCTCAAGAGGGAACTTCTCTGAACTTGAAGAGCTT
     C  G  L  A  A  L  V  I  L  K  R  E  R  S  L  N  L  K  S  L

841  ATTACAATGGGTGACAAGCCGGACAGATGCGATTGAAGGAGGATTTCAGGCCGCTGCAA
     L  Q  W  V  T  S  R  Q  M  R  F  E  G  G  F  Q  G  R  C  N

901  CAAGCTGGTGGATGGCTGCTACTCCTTCTGGCAGGGGCTCCGCCTCCTGCCTCCACCG
     K  L  V  D  G  C  Y  S  F  W  Q  A  G  L  L  P  L  L  H  R

961  CGCACTGCAGCCCAAGGTACACCTGCCTTAGCATGAGCCACTGATGTTCCATCAGCA
     A  L  H  A  Q  G  D  P  A  L  S  M  S  H  W  M  F  H  Q  Q

1021 GGCCCTGCAGGAGTACATCCTGATGTGCTGCCAGTGCCCTGCGGGGGGCTTCTGGATAA
     A  L  Q  E  Y  I  L  M  C  C  Q  C  P  A  G  G  L  L  D  K

FIG. 5B

```
1081  ACCTGGCAAGTCGGTGATTCTACCACACTGCTCCTGAGGGCCTGTCCATAGC
       P  G  K  S  R  D  F  Y  H  T  C  Y  C  L  S  G  L  S  I  A

1141  CCAGCACTTCGGCAGGGAGCCATGTTGCATGATGTGGTCCTGGGTGTGCCGAAAACGC
       Q  H  F  G  S  G  A  M  L  H  D  V  V  L  G  V  P  E  N  A

1201  TCTGCAGCCCACTCACCCAGTACACCATTGGACCAGACAAGGTGATCCAGGCCACTAC
       L  Q  P  T  H  P  V  Y  N  I  G  P  D  K  V  I  Q  A  T  T

1261  ATACTTTCTACAGAAGCCAGTCCCAGTTTGAGGAGCTTAAGGATGAGACATGGCAGA
       Y  F  L  Q  K  P  V  P  G  F  E  E  L  K  D  E  T  S  A  E

1321  GCCTGCAACCGACGAGGAGTTTTAACTATGCCTGCTACTGAAGGTGTTGGTGAAGCTGCA
       P  A  T  D  E  E  F  *   M  A  A  T  E  G  V  G  E  A  A

1381  CAGGGTGGTGAGCCCGGGCAGCCGGCACAACCCCCACCGCAACCCCACCGCCCCACCGCCC
       Q  G  G  E  P  G  Q  P  A  Q  P  P  P  Q  P  H  P  P  P  P

1441  CAGCAGCAGCACAAGGAAGAGATGGCGGCGGAGGCTGGGGAAGCGTGGGTCCCCATG
       Q  Q  Q  H  K  E  E  M  A  A  E  A  G  E  A  V  A  S  P  M

1501  GACGACGGGTTTGTGAGCCTGGACTCGCCCTCCTATGTCCTATGTCCTGTACAGGGACAGAGCAGAA
       D  D  G  F  V  S  L  D  S  P  S  Y  V  L  Y  R  D  R  A  E

1561  TGGCCTGATATAGATCCGGTCCCAGAATGATGCCCAATCCGTGTCCAGATCATT
       W  A  D  I  D  P  V  P  Q  N  D  G  P  N  P  V  V  Q  I  I
```

FIG.5C

```
1621  TATAGTGACAAATTTAGAGATGTTTATGATTACTTCCGACTGTCTCCAGGTGATGAA
      Y  S  D  K  F  R  D  V  Y  D  Y  F  R  A  V  L  Q  R  D  E

1681  AGAAGTGAACGAGCTTTTAAGCTAACCCGACTATTGAGTTAAATGACGCCAATTAT
      R  S  E  R  A  F  K  L  T  R  D  A  I  E  L  N  A  A  N  Y

1741  ACAGTGTGGCATTCCGAGAGTTCTTTGAAGTCACTTGCAGAAGATCTACATGAGGAA
      T  V  W  H  F  R  R  V  L  L  K  S  L  Q  K  D  L  H  E  E

1801  ATGAACTACATCACTGCAATAATTGAGGAGCAGCCAAAAACTATCAAGTTTGGCATCAT
      M  N  Y  I  T  A  I  I  E  E  Q  P  K  N  Y  Q  V  W  H  H

1861  AGGCGAGTATTAGTGGAATGGCTAAGAGATCCATCTCAGGAGCTTGAATTTATGCTGAT
      R  R  V  L  V  E  W  L  R  D  P  S  Q  E  L  E  F  I  A  D

1921  ATTCTTAATCAGGATGCAAAGAATTATCATGCTGGCAGATGTGGACCAACTTCTGAAAGAGGATGTG
      I  L  N  Q  D  A  K  N  Y  H  A  W  Q  H  R  Q  W  V  I  Q

1981  GAATTTAAACTTTGGGATAATGAGCTGCAGTATGTGGACCAACTTCTGAAAGAGGATGTG
      E  F  K  L  W  D  N  E  L  Q  Y  V  D  Q  L  L  K  E  D  V

2041  AGAAATAACTCTGTCTGGAACCAAGATACTTCGTTATTCTAACACTGGCTACAAT
      R  N  N  S  V  W  N  Q  R  Y  F  V  I  S  N  T  T  G  Y  N

2101  GATCGTGCTGTATTGGAGAGAAGTCCAATACACTCTGAAATGATTAAACTAGTACCA
      D  R  A  V  L  E  R  E  V  Q  Y  T  L  E  M  I  K  L  V  P
```

FIG. 5D

2161 CATAATGAAAGTGCATGAACTATTTGAAAGGATTTTGCAGGATGTGTGGTCTTCCAAA
H N E S A W N Y L K G I L Q D R G L S K

2221 TATCCTAATCTGTTAAATCAATTACTTGATTACAACCAAGTCATAGTTCCCCTACCTA
Y P N L L N Q L L D L Q P S H S S P Y L

2281 ATTGCCTTTCTTGTGGATATCTATGAAGACATGCTAGAAAATCAGTGTGACAATAAGAA
I A F L V D I Y E D M L E N Q C D N K E

2341 GACATTCTTAATAAGCATTAGAGTTATGTGAAATCTAGCTAAAGAAAAGGACTATA
D I L N K A L E L C E I L A K E K D T I

2401 AGAAAGGAATATATTGGAGATACATTGGAAGATCCCTTCAAAGCAAACACAGACAGAAAAT
R K E Y W R Y I G R S L Q S K H S T E N

2461 GACTCACCAACAAATGTACCAGCAATAAGAATTAATTCGTACCCGGGATCCTCTAGAGT
D S P T N V Q Q *

2521 CTAAGAATTAATTCGATATCAAGCTT 2546

FIG.5E

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:1:

AAGCTTAACC ATGGACGACG GG 22

(2) INFORMATION FOR SEQ ID NO:2:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:2:

ATCCAGGCCA CCACCCACTT CCTGCAGAAG CCT 33

(2) INFORMATION FOR SEQ ID NO:3:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:3:

CTCCTCAAAG CCAGGCACAG GCTTCTGCAG GAA 33

(2) INFORMATION FOR SEQ ID NO:4:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:4:

```
Ile Gln Ala Thr Thr His Phe Leu Gln Lys Pro Val Pro Gly Phe Glu
 1               5                  10                  15
Glu
```

(2) INFORMATION FOR SEQ ID NO:5:

( i ) SEQUENCE CHARACTERISTICS:
        ( A ) LENGTH: 1314 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:5:

```
ATGGCTTCTC CGAGTTCCTT CACCTACTGT TGCCCTCCAT CTTCCTCCCC TATCTGGTCA      60
GAACCGCTGT ACAGTCTGAG GCCAGAGCAC GCGCGGGAGC GGTTGCAGGA CGACTCGGTG     120
GAAACAGTCA CGTCCATAGA ACAGGCAAAA GTAGAAGAAA AGATCCAAGA GGTCTTCAGT     180
TCTTACAAGT TCAACCACCT TGTACCAAGG CTTGTTTTGC AGAGAGAGAA GCACTTCCAT     240
TATCTGAAAA GAGGCCTCCG ACAGCTGACA GATGCCTACG AGTGTCTGGA TGCCAGCCGC     300
CCATGGCTCT GCTACTGGAT CCTGCATAGC CTGGAACTCC TGGATGAGCC CATCCCCCAG     360
ATGGTGGCCA CAGACGTGTG TCAGTTCCTG GAGTTGTGTC AGAGCCCAGA AGGCGGCTTT     420
GGAGGGGGCC CTGGCCAGTA CCCACACCTT GCACCCACGT ATGCAGCGGT CAACGCGCTG     480
TGCATCATTG GCACCGAGGA GGCCTATGAC GTCATTAACA GAGAGAAGCT TCTCCAGTAT     540
TTGTACTCGC TGAAGCAACC CGATGGCTCT TTTCTCATGC ACGATGGAGG TGAGGTGGAC     600
GTGAGAAGTG CATACTGTGC TGCCTCGGTA GCTTCGTTGA CCAACATCAT CACCCCAGAC     660
CTGTTTGAGG GCACTGCTGA ATGGATCGCA AGGTGTCAGA ATTGGAAGG TGGGATTGGC      720
GGGGTACCAG GAATGGAAGC CCATGGCGGC TACACGTTCT GTGGCCTGGC TGCGCTGGTC     780
ATCCTCAAGA AGGAGCGCTC CTTGAACTTG AAGAGCTTAC TACAATGGGT GACAAGCCGG     840
CAGATGAGGT TTGAAGGTGG ATTTCAGGGC CGCTGCAACA AGCTGGTAGA CGGCTGCTAC     900
TCCTTCTGGC AGGCGGGTCT CCTGCCCCTG CTTCACCGCG CGCTGCACGC CCAAGGTGAC     960
CCTGCCCTCA GCATGAGTCG CTGGATGTTT CACCAGCAGG CCCTGCAGGA GTACATCCTG    1020
ATGTGCTGCC AGTGCCCCAC CGGGGGGCTT CTGGACAAAC TGGCAAGTC CCGGGACTTC     1080
TACCACACCT GCTACTGCCT GAGTGGCCTG TCCATAGCCC AGCACTTCGG CAGCGGAGCC    1140
ATGTTGCACG ATGTGGTCTT GGGTGTACCT GAAAACGCCC TGCAGCCCAC TCACCCTGTG    1200
TACAATATTG GACCAGACAA AGTGATCCAG GCTACCATGC ACTTTCTGCA GAAGCCAGTT    1260
CCAGGCTTTG AGGAGCATGA GGATGAGGCA TCAGCAGAGC CTGCCACTGA CTAG          1314
```

( 2 ) INFORMATION FOR SEQ ID NO:6:

( i ) SEQUENCE CHARACTERISTICS:
( A ) LENGTH: 437 amino acids
( B ) TYPE: amino acid
( D ) TOPOLOGY: linear ( i i ) MOLECULE TYPE: protein ( i i i ) HYPOTHETICAL: NO ( v ) FRAGMENT TYPE: N-terminal ( x i ) SEQUENCE DESCRIPTION: SEQ ID NO:6:

```
Met Ala Ser Pro Ser Ser Phe Thr Tyr Cys Cys Pro Pro Ser Ser Ser
  1               5                  10                  15
Pro Ile Trp Ser Glu Pro Leu Tyr Ser Leu Arg Pro Glu His Ala Arg
                 20                  25                  30
Glu Arg Leu Gln Asp Asp Ser Val Glu Thr Val Thr Ser Ile Glu Gln
             35                  40                  45
Ala Lys Val Glu Glu Lys Ile Gln Glu Val Phe Ser Ser Tyr Lys Phe
         50                  55                  60
Asn His Leu Val Pro Arg Leu Val Leu Gln Arg Glu Lys His Phe His
 65                  70                  75                  80
Tyr Leu Lys Arg Gly Leu Arg Gln Leu Thr Asp Ala Tyr Glu Cys Leu
                 85                  90                  95
```

Asp Ala Ser Arg Pro Trp Leu Cys Tyr Trp Ile Leu His Ser Leu Glu
            100                 105                 110

Leu Leu Asp Glu Pro Ile Pro Gln Met Val Ala Thr Asp Val Cys Gln
            115                 120                 125

Phe Leu Glu Leu Cys Gln Ser Pro Glu Gly Gly Phe Gly Gly Gly Pro
        130                 135                 140

Gly Gln Tyr Pro His Leu Ala Pro Thr Tyr Ala Ala Val Asn Ala Leu
145                     150                 155                 160

Cys Ile Ile Gly Thr Glu Glu Ala Tyr Asp Val Ile Asn Arg Glu Lys
                165                 170                 175

Leu Leu Gln Tyr Leu Tyr Ser Leu Lys Gln Pro Asp Gly Ser Phe Leu
            180                 185                 190

Met His Asp Gly Gly Glu Val Asp Val Arg Ser Ala Tyr Cys Ala Ala
            195                 200                 205

Ser Val Ala Ser Leu Thr Asn Ile Ile Thr Pro Asp Leu Phe Glu Gly
        210                 215                 220

Thr Ala Glu Trp Ile Ala Arg Cys Gln Asn Trp Glu Gly Gly Ile Gly
225                     230                 235                 240

Gly Val Pro Gly Met Glu Ala His Gly Gly Tyr Thr Phe Cys Gly Leu
                245                 250                 255

Arg Ala Leu Val Ile Leu Lys Lys Glu Arg Ser Leu Asn Leu Lys Ser
            260                 265                 270

Leu Leu Gln Trp Val Thr Ser Arg Gln Met Arg Phe Glu Gly Gly Phe
        275                 280                 285

Gln Gly Arg Cys Asn Lys Leu Val Asp Gly Cys Tyr Ser Phe Trp Gln
    290                 295                 300

Ala Gly Leu Leu Pro Leu Leu His Arg Ala Leu His Ala Gln Gly Asp
305                     310                 315                 320

Pro Ala Leu Ser Met Ser Arg Trp Met Phe His Gln Gln Ala Leu Gln
                325                 330                 335

Glu Tyr Ile Leu Met Cys Cys Gln Cys Pro Thr Gly Gly Leu Leu Asp
            340                 345                 350

Lys Pro Gly Lys Ser Arg Asp Phe Tyr His Thr Cys Tyr Cys Leu Ser
        355                 360                 365

Gly Leu Ser Ile Ala Gln His Phe Gly Ser Gly Ala Met Leu His Asp
    370                 375                 380

Val Val Leu Gly Val Pro Glu Asn Ala Leu Gln Pro Thr His Pro Val
385                     390                 395                 400

Tyr Asn Ile Gly Pro Asp Lys Val Ile Gln Ala Thr Met His Phe Leu
                405                 410                 415

Gln Lys Pro Val Pro Gly Phe Glu Glu His Glu Asp Glu Ala Ser Ala
            420                 425                 430

Glu Pro Ala Thr Asp
            435

( 2 ) INFORMATION FOR SEQ ID NO:7:

( i ) SEQUENCE CHARACTERISTICS:
        ( A ) LENGTH: 1140 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO (i v) ANTI-SENSE: NO (x i) SEQUENCE DESCRIPTION: SEQ ID NO:7:

| | | | | | | |
|---|---|---|---|---|---|---|
| ATGGCGGCCA | CCGAGGGGGT | CGGGGAGGCT | GCGCAAGGGG | GCGAGCCCGG | GCAGCCGGCG | 60 |
| CAACCCCCGC | CCCAGCCGCA | CCCACCGCCG | CCCCAGCAGC | AGCACAAGGA | AGAGATGGCG | 120 |
| GCCGAGGCTG | GGGAAGCCGT | GGCGTCCCCC | ATGGACGACG | GGTTTGTGAG | CCTGGACTCG | 180 |
| CCCTCCTATG | TCCTGTACAG | GGACAGAGCA | GAATGGGCTG | ATATAGATCC | GGTGCCGCAG | 240 |
| AATGATGGCC | CCAATCCCGT | GGTCCAGATC | ATTTATAGTG | ACAAATTTAG | AGATGTTTAT | 300 |
| GATTACTTCC | GAGCTGTCCT | GCAGCGTGAT | GAAAGAAGTG | AACGAGCTTT | TAAGCTAACC | 360 |
| CGGGATGCTA | TTGAGTTAAA | TGCAGCCAAT | TATACAGTGT | GGCATTTCCG | GAGAGTTCTT | 420 |
| TTGAAGTCAC | TTCAGAAGGA | TCTACATGAG | GAAATGAACT | ACATCACTGC | AATAATTGAG | 480 |
| GAGCAGCCCA | AAAACTATCA | AGTTTGGCAT | CATAGGCGAG | TATTAGTGGA | ATGGCTAAGA | 540 |
| GATCCATCTC | AGGAGCTTGA | ATTTATTGCT | GATATTCTTA | ATCAGGATGC | AAAGAATTAT | 600 |
| CATGCCTGGC | AGCATCGACA | ATGGGTTATT | CAGGAATTTA | AACTTTGGGA | TAATGAGCTG | 660 |
| CAGTATGTGG | ACCAACTTCT | GAAAGAGGAT | GTGAGAAATA | ACTCTGTCTG | GAACCAAAGA | 720 |
| TACTTCGTTA | TTTCTAACAC | CACTGGCTAC | AATGATCGTG | CTGTATTGGA | GAGAGAAGTC | 780 |
| CAATACACTC | TGGAAATGAT | TAAACTAGTA | CCACATAATG | AAAGTGCATG | GAACTATTTG | 840 |
| AAAGGGATTT | TGCAGGATCG | TGGTCTTTCC | AAATATCCTA | ATCTGTTAAA | TCAATTACTT | 900 |
| GATTTACAAC | CAAGTCATAG | TTCCCCCTAC | CTAATTGCCT | TTCTTGTGGA | TATCTATGAA | 960 |
| GACATGCTAG | AAAATCAGTG | TGACAATAAG | GAAGACATTC | TTAATAAAGC | ATTAGAGTTA | 1020 |
| TGTGAAATCC | TAGCTAAAGA | AAAGGACACT | ATAAGAAAGG | AATATTGGAG | ATACATTGGA | 1080 |
| AGATCCCTTC | AAAGCAAACA | CAGCACAGAA | AATGACTCAC | CAACAAATGT | ACAGCAATAA | 1140 |

(2) INFORMATION FOR SEQ ID NO:8:

(i) SEQUENCE CHARACTERISTICS:
        (A) LENGTH: 379 amino acids
        (B) TYPE: amino acid
        (C) STRANDEDNESS: single
        (D) TOPOLOGY: linear (i i) MOLECULE TYPE: protein (i i i) HYPOTHETICAL: NO (v) FRAGMENT TYPE: N-terminal (x i) SEQUENCE DESCRIPTION: SEQ ID NO:8:

```
Met Ala Ala Thr Glu Gly Val Gly Glu Ala Ala Gln Gly Gly Glu Pro
 1               5                  10                  15

Gly Gln Pro Ala Gln Pro Pro Gln Pro His Pro Pro Pro Pro Gln
            20                  25                  30

Gln Gln His Lys Glu Glu Met Ala Ala Glu Ala Gly Glu Ala Val Ala
            35                  40                  45

Ser Pro Met Asp Asp Gly Phe Val Ser Leu Asp Ser Pro Ser Tyr Val
        50                  55                  60

Leu Tyr Arg Asp Arg Ala Glu Trp Ala Asp Ile Asp Pro Val Pro Gln
65                  70                  75                  80

Asn Asp Gly Pro Asn Pro Val Val Gln Ile Ile Tyr Ser Asp Lys Phe
                85                  90                  95

Arg Asp Val Tyr Asp Tyr Phe Arg Ala Val Leu Gln Arg Asp Glu Arg
                100                 105                 110
```

| | | | | | | | | | | | | | | |
|---|---|---|---|---|---|---|---|---|---|---|---|---|---|---|
|Ser|Glu|Arg|Ala|Phe|Lys|Leu|Thr|Arg|Asp|Ala|Ile|Glu|Leu|Asn|Ala|
| | |115| | | |120| | | |125| | | | |
|Ala|Asn|Tyr|Thr|Val|Trp|His|Phe|Arg|Arg|Val|Leu|Leu|Lys|Ser|Leu|
| |130| | | | |135| | | |140| | | | |
|Gln|Lys|Asp|Leu|His|Glu|Met|Asn|Tyr|Ile|Thr|Ala|Ile|Ile|Glu|
|145| | | | |150| | | |155| | | | |160|
|Glu|Gln|Pro|Lys|Asn|Tyr|Gln|Val|Trp|His|His|Arg|Arg|Val|Leu|Val|
| | | | |165| | | |170| | | | |175| |
|Glu|Trp|Leu|Arg|Asp|Pro|Ser|Gln|Glu|Leu|Glu|Phe|Ile|Ala|Asp|Ile|
| | | |180| | | |185| | | | |190| | |
|Leu|Asn|Gln|Asp|Ala|Lys|Asn|Tyr|His|Ala|Trp|Gln|His|Arg|Gln|Trp|
| | |195| | | |200| | | | |205| | | |
|Val|Ile|Gln|Glu|Phe|Lys|Leu|Trp|Asp|Asn|Glu|Leu|Gln|Tyr|Val|Asp|
| |210| | | |215| | | | |220| | | | |
|Gln|Leu|Leu|Lys|Glu|Asp|Val|Arg|Asn|Asn|Ser|Val|Trp|Asn|Gln|Arg|
|225| | | |230| | | |235| | | | |240| |
|Tyr|Phe|Val|Ile|Ser|Asn|Thr|Thr|Gly|Tyr|Asn|Asp|Arg|Ala|Val|Leu|
| | | |245| | | |250| | | | |255| | |
|Glu|Arg|Glu|Val|Gln|Tyr|Thr|Leu|Glu|Met|Ile|Lys|Leu|Val|Pro|His|
| | |260| | | |265| | | |270| | | | |
|Asn|Glu|Ser|Ala|Trp|Asn|Tyr|Leu|Lys|Gly|Ile|Leu|Gln|Asp|Arg|Gly|
| |275| | | | |280| | | |285| | | | |
|Leu|Ser|Lys|Tyr|Pro|Asn|Leu|Leu|Asn|Gln|Leu|Leu|Asp|Leu|Gln|Pro|
| |290| | | |295| | | |300| | | | | |
|Ser|His|Ser|Ser|Pro|Tyr|Leu|Ile|Ala|Phe|Leu|Val|Asp|Ile|Tyr|Glu|
|305| | | |310| | | |315| | | | |320| |
|Asp|Met|Leu|Glu|Asn|Gln|Cys|Asp|Asn|Lys|Glu|Asp|Ile|Leu|Asn|Lys|
| | | |325| | | |330| | | | |335| | |
|Ala|Leu|Glu|Leu|Cys|Glu|Ile|Leu|Ala|Lys|Glu|Lys|Asp|Thr|Ile|Arg|
| | |340| | | |345| | | |350| | | | |
|Lys|Glu|Tyr|Trp|Arg|Tyr|Ile|Gly|Arg|Ser|Leu|Gln|Ser|Lys|His|Ser|
| |355| | | |360| | | |365| | | | | |
|Thr|Glu|Asn|Asp|Ser|Pro|Thr|Asn|Val|Gln|Gln| | | | | |
|370| | | |375| | | | | | | | | | | |

( 2 ) INFORMATION FOR SEQ ID NO:9:

( i ) SEQUENCE CHARACTERISTICS:
        ( A ) LENGTH: 1314 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:9:

| | | | | | |
|---|---|---|---|---|---|
|ATGGCTTCTC|CGAGTTCTTT|CACCTACTAT|TGCCCTCCAT|CTTCCTCCCC|CGTCTGGTCA|60|
|GAGCCGCTGT|ACAGTCTGAG|GCCCGAGCAC|GCGCGAGAGC|GGTTGCAGGA|CGACTCGGTG|120|
|GAAACAGTCA|CGTCCATAGA|ACAGGCAAAA|GTAGAAGAAA|AGATCCAAGA|GGTCTTCAGT|180|
|TCTTACAAGT|TCAACCACCT|TGTACCAAGG|CTTGTTTTGC|AGAGGGAGAA|GCACTTCCAT|240|
|TATCTGAAAA|GAGGCCTTCG|ACAACTGACA|GATGCCTATG|AGTGTCTGGA|TGCCAGCCGC|300|
|CCATGGCTCT|GCTATTGGAT|CCTGCACAGC|TTGGAACTGC|TAGATGAACC|CATCCCCCAG|360|

-continued

```
ATAGTGGCTA CAGATGTGTG TCAGTTCCTG GAGCTGTGTC AGAGCCCAGA AGGTGGCTTT      420
GGAGGAGGAC CCGGTCAGTA TCCACACCTT GCACCCACAT ATGCAGCAGT CAATGCATTG      480
TGCATCATTG GCACCGAGGA GGCCTATGAC ATCATTAACA GAGAGAAGCT TCTTCAGTAT      540
TTGTACTCCC TGAAGCAACC TGACGGCTCC TTTCTCATGC ATGTCGGAGG TGAGGTGGAT      600
GTGAGAAGCG CATACTGTGC TGCCTCCGTA GCCTCGCTGA CCAACATCAT CACTCCAGAC      660
CTCTTTGAGG GCACTGCTGA ATGGATAGCA AGGTGTCAGA ACTGGGAAGG TGGCATTGGC      720
GGGGTACCAG GGATGGAAGC CCATGGTGGC TATACCTTCT GTGGCCTGGC CGCGCTGGTA      780
ATCCTCAAGA GGGAACGTTC CTTGAACTTG AAGAGCTTAT TACAATGGGT GACAAGCCGG      840
CAGATGCGAT TTGAAGGAGG ATTTCAGGGC CGCTGCAACA AGCTGGTGGA TGGCTGCTAC      900
TCCTTCTGGC AGGCGGGGCT CCTGCCCCTG CTCCACCGCG CACTGCACGC CCAAGGTGAC      960
CCTGCCCTTA GCATGAGCCA CTGGATGTTC CATCAGCAGG CCCTGCAGGA GTACATCCTG     1020
ATGTGCTGCC AGTGCCCTGC GGGGGGGCTT CTGGATAAAC CTGGCAAGTC GCGTGATTTC     1080
TACCACACCT GCTACTGCCT GAGCGGCCTG TCCATAGCCC AGCACTTCGG CAGCGGAGCC     1140
ATGTTGCATG ATGTGGTCCT GGGTGTGCCC GAAAACGCTC TGCAGCCCAC TCACCCAGTG     1200
TACAACATTG GACCAGACAA GGTGATCCAG GCCACTACAT ACTTTCTACA GAAGCCAGTC     1260
CCAGGTTTTG AGGAGCTTAA GGATGAGACA TCGGCAGAGC CTGCAACCGA CTAG           1314
```

( 2 ) INFORMATION FOR SEQ ID NO:10:

( i ) SEQUENCE CHARACTERISTICS:
        ( A ) LENGTH: 437 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v ) FRAGMENT TYPE: N-terminal ( x i ) SEQUENCE DESCRIPTION: SEQ ID NO:10:

```
Met Ala Ser Pro Ser Ser Phe Thr Tyr Tyr Cys Pro Pro Ser Ser Ser
 1               5                  10                 15

Pro Val Trp Ser Glu Pro Leu Tyr Ser Leu Arg Pro Glu His Ala Arg
             20                  25                  30

Glu Arg Leu Gln Asp Asp Ser Val Glu Thr Val Thr Ser Ile Glu Gln
         35                  40                  45

Ala Lys Val Glu Glu Lys Ile Gln Glu Val Phe Ser Ser Tyr Lys Phe
     50                  55                  60

Asn His Leu Val Pro Arg Leu Val Leu Gln Arg Glu Lys His Phe His
 65                  70                  75                  80

Tyr Leu Lys Arg Gly Leu Arg Gln Leu Thr Asp Ala Tyr Glu Cys Leu
                 85                  90                  95

Asp Ala Ser Arg Pro Trp Leu Cys Tyr Trp Ile Leu His Ser Leu Glu
            100                 105                 110

Leu Leu Asp Glu Pro Ile Pro Gln Ile Val Ala Thr Asp Val Cys Gln
        115                 120                 125

Phe Leu Glu Leu Cys Gln Ser Pro Glu Gly Gly Phe Gly Gly Gly Pro
    130                 135                 140

Gly Gln Tyr Pro His Leu Ala Pro Thr Tyr Ala Ala Val Asn Ala Leu
145                 150                 155                 160

Cys Ile Ile Gly Thr Glu Glu Ala Tyr Asp Ile Ile Asn Arg Glu Lys
```

|     |     |     |     | 165 |     |     |     | 170 |     |     |     | 175 |     |     |
|-----|-----|-----|-----|-----|-----|-----|-----|-----|-----|-----|-----|-----|-----|-----|
| Leu | Leu | Gln | Tyr<br>180 | Leu | Tyr | Ser | Leu | Lys<br>185 | Gln | Pro | Asp | Gly | Ser<br>190 | Phe | Leu |
| Met | His | Val<br>195 | Gly | Gly | Glu | Val | Asp<br>200 | Val | Arg | Ser | Ala | Tyr<br>205 | Cys | Ala | Ala |
| Ser | Val<br>210 | Ala | Ser | Leu | Thr | Asn<br>215 | Ile | Ile | Thr | Pro | Asp<br>220 | Leu | Phe | Glu | Gly |
| Thr<br>225 | Ala | Glu | Trp | Ile | Ala<br>230 | Arg | Cys | Gln | Asn | Trp<br>235 | Glu | Gly | Gly | Ile | Gly<br>240 |
| Gly | Val | Pro | Gly | Met<br>245 | Glu | Ala | His | Gly | Gly<br>250 | Tyr | Thr | Phe | Cys | Gly<br>255 | Leu |
| Ala | Ala | Leu | Val<br>260 | Ile | Leu | Lys | Arg | Glu<br>265 | Arg | Ser | Leu | Asn | Leu<br>270 | Lys | Ser |
| Leu | Leu | Gln<br>275 | Trp | Val | Thr | Ser | Arg<br>280 | Gln | Met | Arg | Phe | Glu<br>285 | Gly | Gly | Phe |
| Gln | Gly<br>290 | Arg | Cys | Asn | Lys | Leu<br>295 | Val | Asp | Gly | Cys | Tyr<br>300 | Ser | Phe | Trp | Gln |
| Ala<br>305 | Gly | Leu | Leu | Pro | Leu<br>310 | Leu | His | Arg | Ala | Leu<br>315 | His | Ala | Gln | Gly | Asp<br>320 |
| Pro | Ala | Leu | Ser | Met<br>325 | Ser | His | Trp | Met | Phe<br>330 | His | Gln | Gln | Ala | Leu<br>335 | Gln |
| Glu | Tyr | Ile | Leu<br>340 | Met | Cys | Cys | Gln | Cys<br>345 | Pro | Ala | Gly | Gly | Leu<br>350 | Leu | Asp |
| Lys | Pro | Gly<br>355 | Lys | Ser | Arg | Asp | Phe<br>360 | Tyr | His | Thr | Cys | Tyr<br>365 | Cys | Leu | Ser |
| Gly | Leu<br>370 | Ser | Ile | Ala | Gln | His<br>375 | Phe | Gly | Ser | Gly | Ala<br>380 | Met | Leu | His | Asp |
| Val<br>385 | Val | Leu | Gly | Val | Pro<br>390 | Glu | Asn | Ala | Leu | Gln<br>395 | Pro | Thr | His | Pro | Val<br>400 |
| Tyr | Asn | Ile | Gly | Pro<br>405 | Asp | Lys | Val | Ile | Gln<br>410 | Ala | Thr | Thr | Tyr | Phe<br>415 | Leu |
| Gln | Lys | Pro | Val<br>420 | Pro | Gly | Phe | Glu | Glu<br>425 | Leu | Lys | Asp | Glu | Thr<br>430 | Ser | Ala |
| Glu | Pro | Ala | Thr | Asp<br>435 |     |     |     |     |     |     |     |     |     |     |     |

(2) INFORMATION FOR SEQ ID NO:11:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:11:

TAAGAATTAA TTC                                    13

(2) INFORMATION FOR SEQ ID NO:12:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:12:

GAATTCATGG CTGCTACTGA AGGTGTTGGT GAAGCTGCAC AGGGTGGT            48

(2) INFORMATION FOR SEQ ID NO:13:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:13:

GAATTCATGA CTATGGCTGC TACTGAAGGT GTTGGTGAAG CTGCACAGGG TGGT       54

(2) INFORMATION FOR SEQ ID NO:14:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:14:

GAATTCAACA TG            12

(2) INFORMATION FOR SEQ ID NO:15:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:15:

GAGGAGTTTT AATTAAGAAT TCGATATCAA GCTT            34

(2) INFORMATION FOR SEQ ID NO:16:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO ( i v ) ANTI-SENSE: NO ( x i ) SEQUENCE DESCRIPTION: SEQ ID NO:16:

GAGGAGTTTT AATTAAGAAT TGATATCAAG CTT    33

( 2 ) INFORMATION FOR SEQ ID NO:17:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:17:

GAGGAGTTTT AATTAAGAAT TATTCGATAT CAAGCTT    37

( 2 ) INFORMATION FOR SEQ ID NO:18:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:18:

GAATTCTAAG GAGGAAAAAA AAATG    25

( 2 ) INFORMATION FOR SEQ ID NO:19:

( i ) SEQUENCE CHARACTERISTICS:
        ( A ) LENGTH: 2546 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:19:

```
GAATTCTAAG GAGGAAAAAA AAATGGCTTC TCCGAGTTCT TTCACCTACT ATTGCCCTCC      60

ATCTTCCTCC CCCGTCTGGT CAGAGCCGCT GTACAGTCTG AGGCCCGAGC ACGCGCGAGA     120

GCGGTTGCAG GACGACTCGG TGGAAACAGT CACGTCCATA GAACAGGCAA AGTAGAAGA     180

AAAGATCCAA GAGGTCTTCA GTTCTTACAA GTTCAACCAC CTTGTACCAA GGCTTGTTTT     240

GCAGAGGGAG AAGCACTTCC ATTATCTGAA AAGAGGCCTT CGACAACTGA CAGATGCCTA     300

TGAGTGTCTG GATCGGAGCC GCCCATGGCT CTGCTATTGG ATCCTGCACA GCTTGGAACT     360

GCTAGATGAA CCCATCCCCC AGATAGTGGC TACAGATGTG TGTCAGTTCC TGGAGCTGTG     420

TCAGAGCCCA GAAGGTGGCT TTGGAGGAGG ACCCGGTCAG TATCCACACC TTGCACCCAC     480

ATATGCAGCA GTCAATGCAT TGTGCATCAT TGGCACCGAG GAGGCCTATG ACATCATTAA     540
```

| | | | | | | |
|---|---|---|---|---|---|---|
| CAGAGAGAAG | CTTCTTCAGT | ATTTGTACTC | CCTGAAGCAA | CCTGACGGCT | CCTTTCTCAT | 600 |
| GCATGTCGGA | GGTGAGGTGG | ATGTGAGAAG | CGCATACTGT | GCTGCCTCCG | TAGCCTCGCT | 660 |
| GACCAACATC | ATCACTCCAG | ACCTCTTTGA | GGGCACTGCT | GAATGGATAG | CAAGGTGTCA | 720 |
| GAACTGGGAA | GGTGGCATTG | GCGGGGTACC | AGGGATGGAA | GCCCATGGTG | GCTATACCTT | 780 |
| CTGTGGCCTG | GCCGCGCTGG | TAATCCTCAA | GAGGGAACGT | TCCTTGAACT | TGAAGAGCTT | 840 |
| ATTACAATGG | GTGACAAGCC | GGCAGATGCG | ATTTGAAGGA | GGATTTCAGG | GCCGCTGCAA | 900 |
| CAAGCTGGTG | GATGGCTGCT | ACTCCTTCTG | GCAGGCGGGG | CTCCTGCCCC | TGCTCCACCG | 960 |
| CGCACTGCAC | GCCCAAGGTG | ACCCTGCCCT | TAGCATGAGC | CACTGGATGT | TCCATCAGCA | 1020 |
| GGCCCTGCAG | GAGTACATCC | TGATGTGCTG | CCAGTGCCCT | GCGGGGGGC | TTCTGGATAA | 1080 |
| ACCTGGCAAG | TCGCGTGATT | TCTACCACAC | CTGCTACTGC | CTGAGCGGCC | TGTCCATAGC | 1140 |
| CCAGCACTTC | GGCAGCGGAG | CCATGTTGCA | TGATGTGGTC | CTGGGTGTGC | CCGAAAACGC | 1200 |
| TCTGCAGCCC | ACTCACCCAG | TGTACAACAT | TGGACCAGAC | AAGGTGATCC | AGGCCACTAC | 1260 |
| ATACTTTCTA | CAGAAGCCAG | TCCCAGGTTT | TGAGGAGCTT | AAGGATGAGA | CATCGGCAGA | 1320 |
| GCCTGCAACC | GACGAGGAGT | TTTAACTATG | GCTGCTACTG | AAGGTGTTGG | TGAAGCTGCA | 1380 |
| CAGGGTGGTG | AGCCCGGGCA | GCCGGCGCAA | CCCCGCCCC | AGCCGCACCC | ACCGCCGCCC | 1440 |
| CAGCAGCAGC | ACAAGGAAGA | GATGGCGGCC | GAGGCTGGGG | AAGCCGTGGC | GTCCCCATG | 1500 |
| GACGACGGGT | TTGTGAGCCT | GGACTCGCCC | TCCTATGTCC | TGTACAGGGA | CAGAGCAGAA | 1560 |
| TGGGCTGATA | TAGATCCGGT | GCCGCAGAAT | GATGGCCCCA | ATCCCGTGGT | CCAGATCATT | 1620 |
| TATAGTGACA | AATTTAGAGA | TGTTTATGAT | TACTTCCGAG | CTGTCCTGCA | GCGTGATGAA | 1680 |
| AGAAGTGAAC | GAGCTTTTAA | GCTAACCCGG | GATGCTATTG | AGTTAAATGC | AGCCAATTAT | 1740 |
| ACAGTGTGGC | ATTTCCGGAG | AGTTCTTTTG | AAGTCACTTC | AGAAGGATCT | ACATGAGGAA | 1800 |
| ATGAACTACA | TCACTGCAAT | AATTGAGGAG | CAGCCCAAAA | ACTATCAAGT | TTGGCATCAT | 1860 |
| AGGCGAGTAT | TAGTGGAATG | GCTAAGAGAT | CCATCTCAGG | AGCTTGAATT | TATTGCTGAT | 1920 |
| ATTCTTAATC | AGGATGCAAA | GAATTATCAT | GCCTGGCAGC | ATCGACAATG | GGTTATTCAG | 1980 |
| GAATTTAAAC | TTTGGGATAA | TGAGCTGCAG | TATGTGGACC | AACTTCTGAA | AGAGGATGTG | 2040 |
| AGAAATAACT | CTGTCTGGAA | CCAAAGATAC | TTCGTTATTT | CTAACACCAC | TGGCTACAAT | 2100 |
| GATCGTGCTG | TATTGGAGAG | AGAAGTCCAA | TACACTCTGG | AAATGATTAA | ACTAGTACCA | 2160 |
| CATAATGAAA | GTGCATGGAA | CTATTTGAAA | GGGATTTTGC | AGGATCGTGG | TCTTTCCAAA | 2220 |
| TATCCTAATC | TGTTAAATCA | ATTACTTGAT | TTACAACCAA | GTCATAGTTC | CCCCTACCTA | 2280 |
| ATTGCCTTTC | TTGTGGATAT | CTATGAAGAC | ATGCTAGAAA | ATCAGTGTGA | CAATAAGGAA | 2340 |
| GACATTCTTA | ATAAAGCATT | AGAGTTATGT | GAAATCCTAG | CTAAAGAAAA | GGACACTATA | 2400 |
| AGAAGGAAT | ATTGGAGATA | CATTGGAAGA | TCCCTTCAAA | GCAAACACAG | CACAGAAAAT | 2460 |
| GACTCACCAA | CAAATGTACA | GCAATAAGAA | TTAATTCGGT | ACCCGGGGAT | CCTCTAGAGT | 2520 |
| CTAAGAATTA | ATTCGATATC | AAGCTT | | | | 2546 |

( 2 ) INFORMATION FOR SEQ ID NO:20:

( i ) SEQUENCE CHARACTERISTICS:
        ( A ) LENGTH: 819 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v ) FRAGMENT TYPE: N-terminal ( x i ) SEQUENCE DESCRIPTION: SEQ ID NO:20:

| Met | Ala | Ser | Pro | Ser | Ser | Phe | Thr | Tyr | Tyr | Cys | Pro | Pro | Ser | Ser | Ser |
|---|---|---|---|---|---|---|---|---|---|---|---|---|---|---|---|
| 1 | | | | 5 | | | | | 10 | | | | | 15 | |
| Pro | Val | Trp | Ser | Glu | Pro | Leu | Tyr | Ser | Leu | Arg | Pro | Glu | His | Ala | Arg |
| | | | 20 | | | | 25 | | | | | 30 | | | |
| Glu | Arg | Leu | Gln | Asp | Asp | Ser | Val | Glu | Thr | Val | Thr | Ser | Ile | Glu | Gln |
| | | 35 | | | | | 40 | | | | | 45 | | | |
| Ala | Lys | Val | Glu | Glu | Lys | Ile | Gln | Glu | Val | Phe | Ser | Ser | Tyr | Lys | Phe |
| | 50 | | | | | 55 | | | | | 60 | | | | |
| Asn | His | Leu | Val | Pro | Arg | Leu | Val | Leu | Gln | Arg | Glu | Lys | His | Phe | His |
| 65 | | | | | 70 | | | | | 75 | | | | | 80 |
| Tyr | Leu | Lys | Arg | Gly | Leu | Arg | Gln | Leu | Thr | Asp | Ala | Tyr | Glu | Cys | Leu |
| | | | | 85 | | | | | 90 | | | | | 95 | |
| Asp | Ala | Ser | Arg | Pro | Trp | Leu | Cys | Tyr | Trp | Ile | Leu | His | Ser | Leu | Glu |
| | | | | 100 | | | | | 105 | | | | | 110 | |
| Leu | Leu | Asp | Glu | Pro | Ile | Pro | Gln | Ile | Val | Ala | Thr | Asp | Val | Cys | Gln |
| | | | 115 | | | | | 120 | | | | | 125 | | |
| Phe | Leu | Glu | Leu | Cys | Gln | Ser | Pro | Glu | Gly | Gly | Phe | Gly | Gly | Gly | Pro |
| | | 130 | | | | | 135 | | | | | 140 | | | |
| Gly | Gln | Tyr | Pro | His | Leu | Ala | Pro | Thr | Tyr | Ala | Ala | Val | Asn | Ala | Leu |
| 145 | | | | | 150 | | | | | 155 | | | | | 160 |
| Cys | Ile | Ile | Gly | Thr | Glu | Glu | Ala | Tyr | Asp | Ile | Ile | Asn | Arg | Glu | Lys |
| | | | | 165 | | | | | 170 | | | | | 175 | |
| Leu | Leu | Gln | Tyr | Leu | Tyr | Ser | Leu | Lys | Gln | Pro | Asp | Gly | Ser | Phe | Leu |
| | | | | 180 | | | | | 185 | | | | | 190 | |
| Met | His | Val | Gly | Gly | Glu | Val | Asp | Val | Arg | Ser | Ala | Tyr | Cys | Ala | Ala |
| | | 195 | | | | | 200 | | | | | 205 | | | |
| Ser | Val | Ala | Ser | Leu | Thr | Asn | Ile | Ile | Thr | Pro | Asp | Leu | Phe | Glu | Gly |
| | 210 | | | | | 215 | | | | | 220 | | | | |
| Thr | Ala | Glu | Trp | Ile | Ala | Arg | Cys | Gln | Asn | Trp | Glu | Gly | Gly | Ile | Gly |
| 225 | | | | | 230 | | | | | 235 | | | | | 240 |
| Gly | Val | Pro | Gly | Met | Glu | Ala | His | Gly | Gly | Tyr | Thr | Phe | Cys | Gly | Leu |
| | | | | 245 | | | | | 250 | | | | | 255 | |
| Ala | Ala | Leu | Val | Ile | Leu | Lys | Arg | Glu | Arg | Ser | Leu | Asn | Leu | Lys | Ser |
| | | | 260 | | | | | 265 | | | | | 270 | | |
| Leu | Leu | Gln | Trp | Val | Thr | Ser | Arg | Gln | Met | Arg | Phe | Glu | Gly | Gly | Phe |
| | | | 275 | | | | | 280 | | | | | 285 | | |
| Gln | Gly | Arg | Cys | Asn | Lys | Leu | Val | Asp | Gly | Cys | Tyr | Ser | Phe | Trp | Gln |
| | | 290 | | | | | 295 | | | | | 300 | | | |
| Ala | Gly | Leu | Leu | Pro | Leu | Leu | His | Arg | Ala | Leu | His | Ala | Gln | Gly | Asp |
| 305 | | | | | 310 | | | | | 315 | | | | | 320 |
| Pro | Ala | Leu | Ser | Met | Ser | His | Trp | Met | Phe | His | Gln | Gln | Ala | Leu | Gln |
| | | | | 325 | | | | | 330 | | | | | 335 | |
| Glu | Tyr | Ile | Leu | Met | Cys | Cys | Gln | Cys | Pro | Ala | Gly | Gly | Leu | Leu | Asp |
| | | | | 340 | | | | | 345 | | | | | 350 | |
| Lys | Pro | Gly | Lys | Ser | Arg | Asp | Phe | Tyr | His | Thr | Cys | Tyr | Cys | Leu | Ser |
| | | | | 355 | | | | | 360 | | | | | 365 | |
| Gly | Leu | Ser | Ile | Ala | Gln | His | Phe | Gly | Ser | Gly | Ala | Met | Leu | His | Asp |
| | | 370 | | | | | 375 | | | | | 380 | | | |
| Val | Val | Leu | Gly | Val | Pro | Glu | Asn | Ala | Leu | Gln | Pro | Thr | His | Pro | Val |
| 385 | | | | | 390 | | | | | 395 | | | | | 400 |

-continued

```
Tyr Asn Ile Gly Pro Asp Lys Val Ile Gln Ala Thr Thr Tyr Phe Leu
            405             410                 415
Gln Lys Pro Val Pro Gly Phe Glu Glu Leu Lys Asp Glu Thr Ser Ala
            420             425                 430
Glu Pro Ala Thr Asp Glu Glu Phe Met Ala Ala Thr Gly Val Gly
            435             440                 445
Glu Ala Ala Gln Gly Gly Glu Pro Gly Gln Pro Ala Gln Pro Pro Pro
    450                 455                 460
Gln Pro His Pro Pro Pro Gln Gln Gln His Lys Glu Glu Met Ala
465                 470                 475                 480
Ala Glu Ala Gly Glu Ala Val Ala Ser Pro Met Asp Asp Gly Phe Val
                    485                 490                 495
Ser Leu Asp Ser Pro Ser Tyr Val Leu Tyr Arg Asp Arg Ala Glu Trp
                500                 505                 510
Ala Asp Ile Asp Pro Val Pro Gln Asn Asp Gly Pro Asn Pro Val Val
            515                 520                 525
Gln Ile Ile Tyr Ser Asp Lys Phe Arg Asp Val Tyr Asp Tyr Phe Arg
    530                 535                 540
Ala Val Leu Gln Arg Asp Glu Arg Ser Glu Arg Ala Phe Lys Leu Thr
545                 550                 555                 560
Arg Asp Ala Ile Glu Leu Asn Ala Ala Asn Tyr Thr Val Trp His Phe
                565                 570                 575
Arg Arg Val Leu Leu Lys Ser Leu Gln Lys Asp Leu His Glu Glu Met
            580                 585                 590
Asn Tyr Ile Thr Ala Ile Ile Glu Glu Gln Pro Lys Asn Tyr Gln Val
        595                 600                 605
Trp His His Arg Arg Val Leu Val Glu Trp Leu Arg Asp Pro Ser Gln
    610                 615                 620
Glu Leu Glu Phe Ile Ala Asp Ile Leu Asn Gln Asp Ala Lys Asn Tyr
625                 630                 635                 640
His Ala Trp Gln His Arg Gln Trp Val Ile Gln Glu Phe Lys Leu Trp
                645                 650                 655
Asp Asn Glu Leu Gln Tyr Val Asp Gln Leu Leu Lys Glu Asp Val Arg
            660                 665                 670
Asn Asn Ser Val Trp Asn Gln Arg Tyr Phe Val Ile Ser Asn Thr Thr
            675                 680                 685
Gly Tyr Asn Asp Arg Ala Val Leu Glu Arg Glu Val Gln Tyr Thr Leu
    690                 695                 700
Glu Met Ile Lys Leu Val Pro His Asn Glu Ser Ala Trp Asn Tyr Leu
705                 710                 715                 720
Lys Gly Ile Leu Gln Asp Arg Gly Leu Ser Lys Tyr Pro Asn Leu Leu
                725                 730                 735
Asn Gln Leu Leu Asp Leu Gln Pro Ser His Ser Ser Pro Tyr Leu Ile
            740                 745                 750
Ala Phe Leu Val Asp Ile Tyr Glu Asp Met Leu Glu Asn Gln Cys Asp
            755                 760                 765
Asn Lys Glu Asp Ile Leu Asn Lys Ala Leu Glu Leu Cys Glu Ile Leu
    770                 775                 780
Ala Lys Glu Lys Asp Thr Ile Arg Lys Glu Tyr Trp Arg Tyr Ile Gly
785                 790                 795                 800
Arg Ser Leu Gln Ser Lys His Ser Thr Glu Asn Asp Ser Pro Thr Asn
                805                 810                 815
Val Gln Gln
```

( 2 ) INFORMATION FOR SEQ ID NO:21:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:21:

Met  Ala  Ala  Gly
    1

( 2 ) INFORMATION FOR SEQ ID NO:22:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:22:

Met  Ala  Ala  Thr  Glu  Gly  Val  Gly  Glu  Ala  Ala  Gln  Gly  Gly
    1                      5                              10

GENES FOR THE SUBUNITS OF HUMAN FARNESYL-PROTEIN TRANSFERASE

RELATED APPLICATIONS

The present patent application is a 371 filing of PCT International U.S. Ser. No. 93/10442, filed Oct. 29, 1993, published as WO94/10184 May 11, 1994, which is a continuation application of application Ser. No. 07/968,782, filed Oct. 30, 1992 now abandoned.

BACKGROUND OF THE INVENTION

The ras gene is found activated in many human cancers, including colorectal carcinoma, exocrine pancreatic carcinoma, and myeloid leukemias. Biological and biochemical studies of Ras action indicate that Ras functions like a G-regulatory protein, since ras must be localized in the plasma membrane and must bind with GTP in order to transform cells (Gibbs, J. et al., *Microbiol. Rev.*, 53, 171–286 (1989)). Forms of ras in cancer cells have mutations that distinguish the encoded protein from Ras in normal cells.

At least 3 post-translational modifications are involved with Ras membrane localization, and all 3-modifications occur at the C-terminus of Ras. The Ras C-terminus contains a sequence motif termed a "CAAX" or "Cys-Aaa1-Aaa2-Xaa" box (Aaa is an aliphatic amino acid and Xaa is any amino acid) (Willumsen et al., *Nature*, 310, 583–586(1984)). Other proteins having this motif include the Ras-related GTP-binding proteins such as Rho, fungal mating factors, the nuclear lamins, and the gamma subunit of transducin.

Farnesyl-protein transferase (FPTase) catalyzes the addition of the isoprenoid farnesyl, from farnesyl diphosphate, to a cysteine residue of such protein substrates having the CAAX terminus (Reiss, Y., Goldstein, J. L., Seabra, M. C., Casey, P. J. and Brown, M. S. (1990) *Cell* 62, 81–88; Schaber, M. D., O'Hara, M. B., Garsky, V. M., Moser, S. D., Bergstrom, J. D., Moores, S. L., Marshall. M. S., Friedman, P. A., Dixon, R. A. F. and Gibbs, J. B. (1990) *J. Biol. Chem.* 265, 14701–14704; Manne, V., Roberts, D., Tobin, A., O'Rourke, E., De Virgilio, M., Meyers, C., Ahmed, N., Kurz, B., Resh, M., Kung, H.-F. and Barbacid, M. (1990) *Proc. Natl. Acad. Sci. U.S.A.* 87, 7541–7545). Farnesylation of Ras facilitates its membrane binding which is essential for efficient cell transformation by oncogenic forms of Ras (Willumsen, B. M., Norris, K., Papageorge, A. G., Hubbert, N. L. and Lowy, D. R. (1984) *EMBO J.* 3, 2581–2584). Thus, inhibitors of FPTase may be antitumor agents. CAAX tetrapeptides are substrates for FPTase with kinetic properties similar to polypeptide substrates indicating that the critical determinants required for enzyme recognition are contained within the CAAX box (Reiss et al., *Cell*, supra; Schaber et al., *J. Biol. Chem.*, supra; Pompliano, D. L., Rands, E., Schaber, M. d., Mosser, S. D., Anthony, N. J. and Gibbs, J. B. (1992) *Biochem.* 31, 3800–3807; Goldstein, J. L. Brown, M. S., Stradley, S. J., Reiss, Y. and Gierasch, L. M. (1991) *J. Biol. Chem.* 266, 15575–15578).

Mammalian FPTase is an αβ heterodimeric protein. Complementary DNAs encoding part or all of the α subunit of FPTase from bovine and rat brain have been isolated (Kohl, N. E. et al., (1991) *J. Biol. Chem.* 266, 18884–18888; Chen et al. (1991) *Cell*, 66, 327–334; Chen et al. (1991) *Proc. Natl. Acad. Sci. U.S.A.* 88, 11368–11372). The proteins that they encode share >95% amino acid sequence identity with one another and 30% identity with the RAM2-encoded subunit of *Saccharomyces cerevisiae* FPTase (He, B. et al. (1991) *Proc. Natl. Acad. Sci. U.S.A.* 88, 11373–11377; Kohl et al., supra). A cDNA encoding the β subunit of rat brain FPTase has been isolated and the protein it encodes shares 37% amino acid sequence identity with the DPR1/RAM1 (RAM1) encoded subunit of *S. cerevisiae* FPTase (Goodman, L. E. et al. (1988) *Yeast*, 4, 271–281; Chen et al. (1991) *Cell*, 66, 327–334) However these cDNAs have not been used for expression of the complete FPTase that is readily isolatable in large quantities.

Previously, amounts of FPTase useful in assessing the inhibitory activity of pharmaceutical agents have been isolated from animal tissue such as rat or bovine brain. However, relatively low amounts of FPTase are present in rat and bovine brain and purification of the enzyme involves a number of separation steps.

Human FPTase, the ideal enzyme to employ in an assay directed at discovering a human anticancer agent, has not been employed previously because of the limited amounts of human FPTase available from human cell culture lines and human tissue and the hazards of working with human cells and tissue.

SUMMARY OF THE INVENTION

The instant invention provides a transformed bacterial cell line capable of expressing a modified mammalian farnesyl-protein transferase (FPTase) especially human farnesyl-protein transferase.

The instant invention also provides a method of preparing and purifying a mammalian FPTase in experimentally useful quantities which comprises expressing the modified mammalian farnesyl-protein transferase and purifying the modified FPTase on an antibody column.

The instant invention also provides an assay useful for the determination of FPTase inhibitory activity of pharmaceutical agents which comprises contacting the pharmaceutical agent to be assessed with substantially pure mammalian FPTase.

BRIEF DESCRIPTION OF THE FIGURES

FIGS. 1A,1B,1C: DNA sequence of the bovine cDNA that encodes the β subunit of bovine brain FPTase enzyme. The numbering of the DNA sequence is on the left of each line of DNA sequence. The numbering of the amino acid sequence is at the right of each line of amino acid sequence.

FIGS. 2A,2B,2C: DNA sequence of the human cDNA that encodes the α subunit of human FPTase enzyme. The numbering of the DNA sequence is on the left of each line of DNA sequence. The numbering of the amino acid sequence is at the right of each line of amino acid sequence.

FIGS. 3A,3B,3C: DNA sequence of the human cDNA that encodes the β subunit of human FPTase enzyme. The numbering of the DNA sequence is on the left of each line of DNA sequence. The numbering of the amino acid sequence is at the right of each line of amino acid sequence.

FIGS. 5A,5B,5C,5D,5E: DNA sequence of the insert used to generate the pRD516 plasmid which incorporates the human cDNAs that encode the α and β subunits of human FPTase enzyme. The numbering of the DNA sequence is on the left of each line of DNA sequence. The numbering of the amino acid sequence is at the right of each line of amino acid sequence.

DETAILED DESCRIPTION OF THE INVENTION

Figure 4:
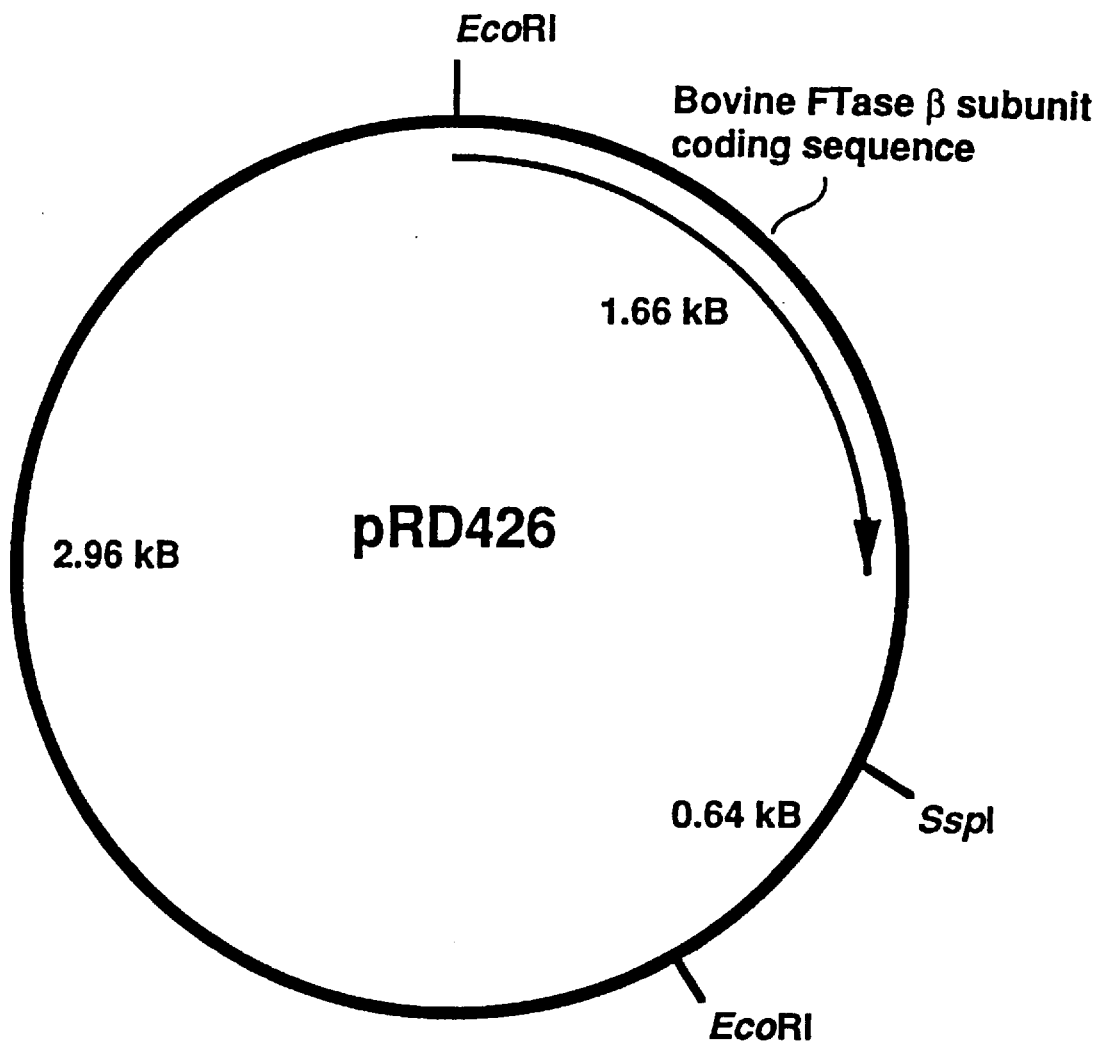
FIG. 4: The plasmid, pRD426, which contains a cDNA sequence encoding the β subunit of bovine FPTase. The restriction sites for the enzymes EcoRI and SspI are indicated. The distances between the restriciton sites are indicated in kilobases (kB). The part of the plasmid encoding the β subunit of bovine FPTase is also indicated by an arc.

A bacterial cell is transformed with a plasmid containing cDNAs encoding α and β subunits of a mammalian FPTase operationally linked by codons in one subunit which contain the ribosomal binding site necessary for translation of the other subunit by the bacterial cell.

The bacterial cell may be any cell capable of expressing the translationally coupled FPTase subunits. Such a cell line may be selected from strains of *Escherichia coli*, such as DH5, HB101, BL21(DE3) and the like.

The cDNAs encoding the α and β subunits of a mammalian FPTase may be selected from subunits such as the a and β subunits of human FPTase, bovine FPTase or rat FPTase and the like. The cDNA encoding an α subunit of one of the mammalian FPTases, for example human FPTase, may be combined with the cDNA encoding the β subunit of a different mammalian FPTase, for instance bovine FPTase. The preferred combination of cDNAs is the cDNAs encoding for the α and β subunits of human FPTase.

The plasmid vector into which the cDNAs encoding the α and β subunits of a mammalian FPTase are cloned may be any vector compatable with transformation into the selected bacterial cell line. Such vectors include, but are not limited to, derivatives of ColE1 (such as pBR322, pUC8, pUC9, pUC18, pUC19, and the like) (Yanish-Perron et al, 1985, *Gene*, 33:103–119) or P15a (such as pACYC177, pACYC184, and the like) (A. C. Y. C. Chang and S. N. Cohen, 1978, *J. Bacteriology*, 134:1141–1156). To operationally link the cDNAs encoding the α and β subunits of a mammalian FPTase to the plasmid, a promoter sequence is necessary. Such promoters include, but are not limited to, the tac promoter (E. Ammon et al., 1983, *Gene*, 25:167–178), lac promoter (U. Siebenlist etal., 1980, *Cell*, 20: 269–281) and trp promoter (G. N. Bennet et al., 1978, *J. Mol. Biol.*, 121:113–137). Such promoters use *E. coli* RNA polymerase to transcribe DNA into mRNA. In one embodiment of the instant invention the promoter is the tac promoter found in the plasmid pBTac1 (commercially available from Boehringer Mannheim Biochemicals). Other promoter/RNA polymerase systems useful in carrying out the instant invention include DNA bacteriophage promoters and their cognate RNA polymerase. Examples of such systems include the bacteriophage T7 promoter and T7 RNA polymerase (F. W. Studier and B. A. Moffat, 1986, *J. Mol. Biol.*, 189: 113–130). It is expected that the bacteriophage T7 promoter and RNA polymerase would give higher levels of protein expression than the tac promoter.

To ensure translation of the transcribed cDNA sequences, a ribosomal binding site must be operationally linked to the FPTase α and β subunit coding sequences. An example of a ribosomal binding site for the β subunit is GGAGG while a ribosomal binding for the α subunit is GGAG encoded in the Glu-Glu-Phe epitope tag which can be placed at the C-terminal end of the β subunit coding sequence.

The transformed cell line is grown and harvested and the mammalian FPTase expressed by the cells is isolated and purified. Isolation and purification of the mammalian FPTase may be accomplished by any of the techniques well known to persons skilled in the art. Preferably an epitope tag is incorporated in the FPTase when it is expressed and the cell lysate is exposed to a column containing an antibody which binds to the tagging amino acid sequence. Most preferably the FPTase is tagged with a C-terminal EEF epitope and the column utilized is a column containing monoclonal antibody YL1/2 (described in J. V. Kilmartin et al., *J. Cell Biology*, 93: 576–582(1982)).

The purified, recombinantly expressed, mammalian FPTase is employed in an assay to determine the inhibitory activity against FPTase mediated farnesylation of Ras by various pharmaceutical compounds. Ras protein is exposed to a labelled farnesyl diphosphate, such as [$^3$H]farnesyl diphosphate and the like, in the presence of the pharmaceutical compound whose activity is to be determined and in a suitable incubation medium, such as a mixture of 50 mM HEPES (pH 7.5), 5 mM $MgCl_2$ and 1–2 mM dithiothreitol, and the like. The purified mammalian FPTase is then added to the assay mixture and the assay mixture is incubated for a period of time such as 10–30 minutes at 30° C. The assay mixture is then quenched and the Ras protein is separated from free FPP by techniques well known in the art. (see for example M. D. Schaber et al. (1990) *J. Biol. Chem.* 265, 14701–14704 and S. L. Moores et al. (1991), *J. Biol. Chem.*, 266: 14603–14610) The isolated Ras protein is then analyzed by a scintillation counting technique to provide a relative value for the amount of Ras protein that had been farnesylated. This value may be compared to the relative value of the amount of Ras farnesylated in the absence of the pharmaceutical agent and to the relative value of the amount of Ras farnesylated in the presence of other pharmaceutical agents.

The invention is further defined by reference to the following examples, which are illustrative and not limiting. All temperatures are in degrees Celsius.

EXAMPLE 1

Labelled Probe from cDNA Encoding for the α Subunit of Bovine FPTase

A probe is used comprising an approximately 1000 bp DNA fragment that spans the open reading frame of the α subunit of bovine FPTase described by Kohl et al. *J. Biol. Chem.* 266, 18884–18888 (1991). This fragment was made by polymerase chain reaction (PCR) and has as its ends: (5' end: seq ID 1)

AAGCTT-AACC-ATG-GAC-GAC-GGG---α subunit---T(AA-
HindIII        Met  Ala  Ala  Gly  (seq ID 21)  Stop
GCTT)
Hind III

EXAMPLE 2 cDNA Encoding for the β Subunit of Bovine FPTase

Two overlapping, complimentary oligonucleotides 5'-ATCCAGGCCACCACCCACTTCCTGCAGAAGCCT 3' (seq ID 2) and 5'-CTCCTCAAAGCCAGGCACAGGCTTCTGCAGGAA-3' (seq ID 3) were made based on codon preferrence usage (Lathe, R. (1985) *J. Mol. Biol.* 183, 1–12) for the codons of the peptide IQATTHFLQKPVPGFEE (seq ID 4) from the β subunit of rat brain FPTase (Reiss, Y., Seabra, M. C., Armstrong, S. A., Slaughter, C. A., Goldstein, J. L. and Brown, M. S. *J. Biol. Chem.* 266, 10672–10677 (1991)). These two oligonucleotides were annealed and filled in with the Klenow fragment of DNA polymerase and all four [$^{32}$P]-labelled deoxynucleotide triphosphates for use as a probe. The double stranded fragment was then heated to separate the strands. A bovine brain oligo(dT) primed cDNA library in λgt10 was screened using the plaque hybridization method and employing this probe. Filters from plaque lifts of the bovine brain cDNA library were prehybridized and hybridized in 5× SSC, 10× Denhardt's solution (1× Denhardt's solution is 20 mg/ml bovine serum albumin, 20 mg/ml polyvinylpyrollidone, 20 mg/ml Ficoll), 0.1% (wt./vol.) SDS at 50° C. overnight. The filters were washed in 5×

SSC at 50° C. and autoradiographed. Positive plaques were selected, grown up and the DNA analyzed by restriction and sequence analysis.

EXAMPLE 3
Labelled Probe from cDNA Encoding for the β Subunit of Bovine FPTase A probe comprising an approximately 1660 bp EcoRI-SspI DNA fragment from pRD426 encoding the bovine β subunit cDNA obtained as described in Example 2 was prepared by restriction digestion. The restriction sites are shown in FIG. 4. The EcoRI site, upstream of the start of the cDNA, comes from the linker used in the cDNA cloning, while the SspI site is approximately 300 bp downstream of the stop codon for the β subunit coding sequence in the nontranslated region of the cDNA. The fragment has the following structure:

<pre>
GAATTC-bp1-61 of cDNA-ATG-β subunit coding seq.-TAG-
EcoRI                   M                      Stop
~300bp-AATATT
       SspI
</pre>

EXAMPLE 4
cDNA Encoding for the α Subunit of Human FPTase

A human placental cDNA library in λgt11 (Clonetech) was probed using the labelled DNA fragment from the bovine FPTase cDNA described in Example 1 above. Filters from the plaque lifts of the human placental cDNA library were prehybridized and hybridized as described in Example 2 except at 65° C. The filters were then washed as described in Example 2 at 65° C. Positive clones from the screens were utilized as described in Example 7 below.

EXAMPLE 5
cDNA Encoding for the β Subunit of Human FPTase

A human placental cDNA library in λgt11 (Clonetech) was probed using the labelled DNA fragment from the bovine FPTase cDNA described in Example 3 above. Filters from the plaque lifts of the human placental cDNA library were prehybridized and hybridized as described in Example 2 except at 65° C. The filters were then washed as described in Example 2 at 65° C. Positive clones from the screens were utilized as described in Example 7 below.

EXAMPLE 6
DNA Sequencing of cDNAs

The cDNAs obtained as described in Examples 2, 4 and 5 were sequenced using the Sequenase II dideoxy sequencing kit (U.S. Biochemical Corp.) as described by the manufacturer using plasmid DNAs as templates. DNA and protein sequence analysis was performed using the Genetics Computer Group software package and the multiple sequence alignment program CLUSTAL (Devereux, J. et al. (1984) *Nucl. Acids Res.* 12, 387–395 and Higgins, D. G. and Sharp, P. M. (1988) *Gene,* 73, 237–244.) DNA subcloning, PCR and other DNA manipulations were performed as described in Maniatis, T., Fritsch, E. F. and Sambrook, J. (1982) *Molecular Cloning: A Laboratory Manual,* Cold Spring Harbor Laboratory, Cold Spring Harbor, N.Y. and Saiki, R. K., Gelfand, D. H., Stoffel, S. Scharf, S. J., Higuchi, R., Horn, G. T., Mullis, K. B. and Erlich, H. A. (1988) *Science* 239, 487–491. The DNA sequences of the FPTase cDNAs were submitted to GenBank and were given the accession numbers L00633 (bovine β subunit) (cDNA: seq ID 5; amino acid: seq ID 6), L00634 (human α subunit) (cDNA: seq ID 7; amino acid: seq ID 8) and L00635 (human β subunit) (cDNA: seq ID 9; amino acid: seq ID 10). FIGS. 1–3 show the respective sequences.

EXAMPLE 7
Construction of Plasmid for Expression of hFPTase in *E. coli*

The coding region of the α subunit of human FPTase was modified by PCR (Saiki et al.) such that EcoRI sites were placed immediately upstream and downstream of the α subunit coding sequence and cloned into pUC18 to create pRD452. The sequence of the insert of pRD452 is as follows:

<pre>
GAATTC-ATG-α codon for aa2-aa379-TAA-GAATTC-(SacI-KpnI-
EcoRI   M                          stop  EcoRI
SmaI-BamHI-HincII-PstI-HindIII)pUC18 polylinker.
</pre> pRD452 was cut with SacI, which only cuts in the polylinker region of the plasmid, the ends were blunted with T4 DNA polymerase and dNTPs and then recircularized. This plasmid was partially digested with EcoRI, the ends filled in with the Klenow fragment of *E. coli* DNA polymerase and dNTPs and recircularized. A plasmid from this step, in which the EcoRI site down stream of the coding sequence of the α subunit of human FPTase was filled in, was identified and is named pRD494. The sequence of the insert in pRD494 is the following: (3' end: seq ID 11)

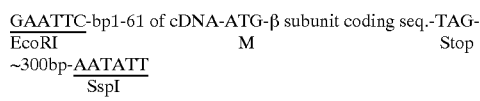
<pre>
GAATTC-ATG-α codon for aa2-aa379-TAA-GAATTAATTC-
EcoRI   M                          stop
(KpnI-SmaI-BamHI-HincII-PstI-SphI-HindIII).
</pre>

The SacI restriction endonuclease site in this plasmid was completely lost. Synthetic oligonucleotides encoding an approximately 70 bp EcoRI-BanII fragment at the 5'-end of the α subunit coding sequence were made that contained primarily A or T at the third position of each codon, and inserted into pRD494 that had been cut with EcoRI and BanII to create pRD493. The sequence of the α subunit coding sequence and the surrounding restriction sites in pRD493 are as follows: (5' end: seq ID 12; 3' end: seq ID 11)

<pre>
GAATTC-ATG GCT GCT ACT GAA GGT GTT GGT GAA GCT
EcoRI   M   A   A   T   E   G   V   G   E   A GCA CAG GGT GGT-codon for aa15-aa379 of the α subunit of
 A   Q   G   G  (seq ID 22)

FPTase-TAA-GAATTAATTC-(KpnI-SmaI-BamHI-HincII-PstI-
           stop
SphI-HindIII)
</pre>

Using PCR, the sequence upstream of the start codon of the α subunit in pRD493 was changed to include a ScaI site immediately upstream of the start codon. The sequence of the α subunit coding sequence and the surrounding restriction sites in pRD515 are as follows: (5' end: seq ID 13; 3' end: seq ID 11)

<pre>
GAATTC-ATGACT-ATG GCT GCT ACT GAA GGT GTT GGT
EcoRI   ScaI   M   A   A   T   E   G   V   G GAA GCT GCA CAG GGT GGT-codon for aa15-aa378 of the α
 E   A   Q   G   G subunit of FPTase-TAA-GAATTAATTC-(KpnI-SmaI-BamHI-
                      stop
HincII-PstI-SphI-HindIII).
</pre>

The 5' end of the cDNA encoding the β subunit of hFPTase was changed using PCR such that an EcoRI site was placed immediately upstream of the coding sequence. The 3' end of the cDNA for the β subunit was changed using PCR such that the codons for Glutamic acid-Glutamic acid-Phenylalanine-stop were placed after the last codon for the β subunit. Additionally, a PacI site was placed spanning the stop codon and an EcoRI site was placed downstream of the PacI restriction site. This EcoRI fragment was cloned into the EcoRI site of pBCKS+ (Stratagene) to make pRD463. The insert and the adjoining sequences in pRD463 are as follows: (5' end: seq ID 14; 3' end: seq ID 15)

GAATTC-AAC-ATG-β subunit hFPTase codons for aa$_2$-aa$_{437}$-
EcoRI     M

GAG-GAG-TTT-TAA-TTAA-GAATTC GATATC AAGCTT
E   E   F  stop  PacI    EcoRI    EcoRV   HindIII The 5' end of the cDNA encoding the β subunit of hFPTase was modified by PCR such that an EcoRI site was placed immediately adjacent to the start codon and a 0.7 kb EcoRI-KpnI fragment containing codons for aa$_1$-aa$_{242}$ of the β subunit was cloned into EcoRI+KpnI cut pUC18 creating pRD464. The ends of the insert in pRD464 are as follows:

GAATTC-ATG-β subunit hFPTase codons for aa$_2$-aa$_{240}$-
EcoRI   M
GGG GTACC
G   KpnI The 0.7 kb EcoRI-KpnI fragment of pRD464 containing the 5' end of the β subunit gene and the 0.6 kb KpnI-HindIII fragment from pRD463 containing the 3' end of the β subunit gene were cloned into the expression vector pBTac1 (Boehringer-Mannheim) that had been cut with EcoRI and HindIII creating pRD466. The ends of the insert in pRD466 are as follows: (3' end: seq ID 16)

tac promoter- RBS-GAATTC-ATG-β subunit hFPTase codons for
                        EcoRI   M aa$_2$-aa$_{437}$-GAG-GAG-TTT-TAA-TTAA-GAATT GATATC
            E   E   F  stop  PacI   EcoRI   EcoRV AAGCTT
HindIII The plasmid pRD466 was partially cleaved with EcoRI and the ends filled in with the Klenow fragment of *E. coli* DNA polymerase and dNTPs, the ends religated and transformed into *E. coli*. A plasmid from this transformation was identified in which the EcoRI site after the β subunit stop codon was filled in, while the EcoRI site upstream of the β subunit coding sequence was intact. The insert in this plasmid, designated pRD478, has the following sequence: (3' end: seq ID 17)

tac promoter- RBS-GAATTC-ATG-β subunit hFPTase codons for
                        EcoRI   M aa$_2$-aa$_{437}$-GAG-GAG-TTT-TAA-TTAA-GAATTATTC-GATATC
            E   E   F  stop  PacI          EcoRV AAGCTT
HindIII The 5' end of the β subunit coding sequence was modified using PCR and a ribosomal binding site (Shine, J. and Dalgarno, L. (1974) *Proc. Natl. Acad. Sci. USA* 71, 1342–1346) was placed between an EcoRI site and the β subunit coding sequence. A 0.3 kb EcoRI-BamHI fragment from this PCR was used to replace the EcoRI-BamHI fragment in pRD478, creating pRD486. The insert in pRD486 has the following sequence: (5' end: seq ID 18; 3' end: seq ID 17)

tac promoter- GAATTC-TAAGGAGGAAAAAAAA-ATG-β subunit
              EcoRI          RBS            M hFPTase codons for aa$_2$-aa$_{437}$-GAG-GAG-TTT-TAA-TTAA-
                              E   E   F  stop  PacI GAATTATTC-GATATC AAGCTT
           EcoRV   HindIII The plasmid pRD486 was cleaved with PacI and the ends blunted with T4 DNA polymerase. This DNA was ligated to a 1.1 kB ScaI-HincII fragment from pRD515 that contained the coding sequence for the α subunit of hFPTase. In the resulting plasmid, pRD516, the coding sequences for the α and β subunits of human FPTase are transcribed on a single mRNA driven by the tac promoter on the plasmid. Translation of the α subunit is coupled (Schoner, B. E., Belagaje, R. M. and Schoner, R. G. (1990) *Methods in Enz.* 185, 94–103) to the translation of the β subunit since the ribosomal binding site (RBS) for the α subunit is the sequence GGAG (Shine, J. and Dalgarno, L., supra) that is within the Glu-Glu-Phe coding sequence appended onto the β subunit coding sequence. The sequence of the DNA fragment containing the coding sequences for the α and β subunits of human FPTase in pRD516 is shown in FIG. 5. (cDNA: seq ID 19; amino acid: seq ID 20).

EXAMPLE 8
Expression and Purification of Human FPTase

To express human FPTase the plasmid pRD516 was transformed into *E. coli* DH5a and grown in LB+100 μg/ml ampicillin at 37° C. until the cultures were in late log to early stationary phase of growth (This culture was deposited on Oct. 14, 1992, with the American Type Culture Collection at 12301 Parklawn Drive, Rockville, Md. 20852 as ATCC-69091). The cells were harvested and FPTase was purified as described below. Human FPTase was isolated from *E. coli* cultures by resuspending a cell pellet in 50 mM Tris-Cl pH7.5, 1 mM EDTA, 1 mM EGTA, 1 mM DTT, 1 mM phenylmethylsulfonyl flouride (PMSF), 2 μg/ml leupeptin, 2 μg/ml antipain, 10 μg/ml aprotinin (approx. 5 g cells/10 ml solution). The resuspended cells were broken by sonication and the cell debris pelleted by centrifugation at 30,000×g at 4° C. for 30 min. The soluble fraction was diluted with an equal volume of 0.15M NaCl, 6 mM NaPO$_4$, pH7.2 (PBS) and applied at a flow rate of approximately 0.5 ml/min to a 2 ml column of the monoclonal antibody YL1/2(4 mg antibody/ml resin) coupled to cyanogen bromide activated Sepharose (Stammers et al.) After loading the protein onto the column, the column was washed with 10–20 ml of ½×PBS containing 2 mM DTT, 0.1% Tween-20, 1 mM PMSF, 2 μg/ml leupeptin, 2 μg/ml antipain, 10 μg/ml aprotinin. The column was then washed with 100–200 ml of ½×PBS containing 2 mM DTT. FPTase was eluted with 3×3 ml of 5 mM Asp-Phe dipeptide (Sigma), 100 mM Tris-Cl pH 7.5, 2 mM DTT. The column was regenerated by washing with PBS+2M NaCl and then storing in PBS+0.02% (wt./vol.) NaN$_3$. The FPTase was obtained in >20% purity and in a 0.1 to 1.0% yield based on the total starting soluble *E. coli* protein. In some cases the FPTase was further purified. This is not necessary for drug screening. To further purify the FPTase he protein eluted from the antibody column was chromatographed by HPLC on a MonoQ HR10-10 column (Pharmacia) where buffer A was 50 mM Tris-Cl pH7.5, 5 mM $MgCl_2$, 5 mM DTT and buffer B was buffer A+1M NaCl. The column was run at 1 ml/min. and the gradient was 0–20% B in 10 min., 20–40% B in 30 min., 40–100% B in 20 min. FPTase eluted at approximately 30–35% B.

EXAMPLE 9
Assay of Purified FPTase Activity in the Absence of Inhibitor

Activity of the purified human FPTase described in Example 8 was assayed in the biosynthetically forward direction at 30° C. Reactions were never allowed to proceed to more than 10% completion based on the limiting substrate. For calculations, the molecular mass of the transferase was assumed to be 93 kD and that of Ras-CVLS to be 21 kD (D. L. Pompliano et al., *Biochem.* 31, 3800–3807 (1992) and S. L. Moores et al. (1991), *J. Biol. Chem.*, 266: 14603–14610)). A typical reaction contained the following: 50 mM HEPES pH7.5, 5 mM $MgCl_2$, 5 mM DTT, 10 mM $ZnCl_2$, 0.1% (wt./vol) polyethylene glycol (ave mol wt. 20000) with [$^3$H]-farnesyl diphosphate (1–3000 nM) and Ras-CVLS protein (20–10000 nM) as substrate. After thermally preequilibrating the asssay mixture in the absence of the enzyme, the reaction was initiated by adding the transferase. Aliquots (50–500 mL) were withdrawn at timed intervals and diluted into 10% HCl in ethanol (1–2 mL). The quenched reaction aliquots were allowed to stand at room temperature for 15 minutes (to hydrolyze unreacted farnesyl diphosphate). After adding 100% ethanol (2 ml), the aliquot workups were vacuum filtered through Whatman GF/C filters using a Brandel cell harvester. Filters were washed four times with 2 mL 100% ethanol, mixed with scintillation fluid (10 mL) and then counted in a Beckman LS3801 scintillation counter. Kinetic data was obtained for the purified human FPTase obtained as described in Example 8 and bovine brain FPTase, obtained as described in S. L. Moores et al.,*J. Biol. Chem.*, 266, 14603 (1991) and is listed in Table 1.

TABLE 1

| FPTase source | FPP $K_m$(nM) | Ras-CVLS $K_m$(nM) | $k_{cat}(s^{-1})$ |
|---|---|---|---|
| human pFPTase-αβ | 9.8 ± 1.7 | 392 ± 20 | 0.010 ± 0.001 |
| bovine brain pFPTase | 9.3 ± 1.0 | 620 ± 80 | 0.013 ± 0.001 |

EXAMPLE 10
Assay of Compounds for FPTase Inhibitory Activity

[$^3$H]Farnesyl diphosphate (FPP) (20 Ci/mmol) was purchased from New England Nuclear. In general, inhibitory activity assays were carried out at 30° C. A typical assay reaction contained (in a final volume of 50 μL): [$^3$H]farnesyl diphosphate, Ras protein (3.5 μM), 50 mM HEPES, pH 7.5, 5 mM $MgCl_2$, 1 mM dithiothreitol, and the compound to be assayed. After thermally preequilibrating the assay mixture, the reaction was initiated by the addition of the purified mammalian FPTase and the reaction was stopped at timed intervals by the addition of 1M HCl in ethanol (1 mL). The quenched reactions were allowed to stand for 15 minutes. After adding 2 mL of 100% ethanol, the mixtures were vacuum filtered through Whatman GF/C filters. Filters were washed four times with 2 mL aliquots of 100% ethanol, mixed with scintillation fluid (10 mL) and then counted in a Beckmann LS3801 scintillation counter. Inhibitory activity values for known compounds in the assay employing the once purified human FPTase and an assay employing bovine brain FPTase are compared in Table 2 below:

TABLE 2

| Inhibitor | $IC_{50}$ value (nM) | |
|---|---|---|
| FTase | Bovine brain FTase | Human |
| tetrapeptide CVIM * | 100 | 100 |
| tetrapeptide CIFM | 10 | 17 |
| tetrapeptide CVIL * | 20,000 | 6,200 |
| unlabelled FPP * | 200 | 250 |
| unlabelled GGPP | 200 | 240 |
| Compound A | 20 | 18 |

* = alternative substrates

CVIM = cysteinyl-valinyl-isolleucinyl-methionine

CIFM = cysteinyl-isolleucinyl-phenylalaninyl-methionine

CVIL = cysteinyl-valinyl-isolleucinyl-leucine

GGPP = geranyl-geranyl-diphosphate

Compound A = (R,S)-[1-hydroxy-(E,E)-3,7,11-trimethyl-2,6,10-dodecatrienyl]phosphonic acid (Pomphiano, D. L. et al., Biochem. 31, 3800–3807 (1992)).

---

What is claimed is:

1. A plasmid operably containing cDNAs encoding an α subunit and a β subunit of a mammalian farnesyl protein transferase which further operably contains a DNA sequence which encodes a glutamic acid-glutamic acid-phenylalanine epitope between the cDNAs that encode the α subunit and β subunit of the mammalian farnesylprotein transferase enzyme, such that the glutamic acid-glutamic acid-phenylalanine epitope is operably linked to one of the subunits upon expression of the plasmid.

2. The plasmid according to claim 1 wherein the mammalian farnesyl protein transferase is human farnesyl protein transferase.

3. The plasmid according to claim 2 wherein the cDNAs are contained in a vector which is pRD516.

4. A bacterium transformed with the plasmid according to claim 3 wherein the bacterium is an *Escherichia coli* and is designated ATCC-69091.

5. A bacterium transformed with the plasmid according to claim 2.

6. A bacterium transformed with the plasmid according to claim 2.

* * * * *